(12) United States Patent
Sherwood et al.

(10) Patent No.: US 7,749,754 B2
(45) Date of Patent: Jul. 6, 2010

(54) ISOLATION AND CHARACTERIZATION OF MUSCLE REGENERATING CELLS

(75) Inventors: Richard Irving Sherwood, Scarsdale, NY (US); Amy Jo Wagers, Boston, MA (US); Irving Weissman, Redwood City, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 670 days.

(21) Appl. No.: 11/149,703

(22) Filed: Jun. 9, 2005

(65) Prior Publication Data

US 2006/0014287 A1    Jan. 19, 2006

Related U.S. Application Data

(60) Provisional application No. 60/578,753, filed on Jun. 9, 2004.

(51) Int. Cl.
*C12N 15/85* (2006.01)
*A61K 48/00* (2006.01)

(52) U.S. Cl. .................. 435/325; 424/93.1

(58) Field of Classification Search ............... None
See application file for complete search history.

(56) References Cited

U.S. PATENT DOCUMENTS

2005/0079606 A1 * 4/2005 Tamaki et al. ............... 435/366

OTHER PUBLICATIONS

Huard J, Cao B, Qu-Petersen Z. Muscle-derived stem cells: potential for muscle regeneration. Birth Defects Res C Embryo Today. Aug. 2003;69(3):230-7. Review.*
Sinanan AC, Buxton PG, Lewis MP. Muscling in on stem cells. Biol Cell. Apr. 2006;98(4):203-14. Review.*
Negroni E, Butler-Browne GS, Mouly V. Myogenic stem cells: regeneration and cell therapy in human skeletal muscle. Pathol Biol (Paris). Mar. 2006;54(2):100-8. Epub Oct. 21, 2005.*
Kucia M, Reca R, Jala VR, Dawn B, Ratajczak J, Ratajczak MZ. Leukemia. Jul. 2005;19(7):1118-27.*
Velleman and McFarland (Poultry Science, 2004, vol. 83, pp. 245-252).*
Ratajczak et al (Stem Cell, 2003. vol. 21, pp. 363-371).*
Le Grand et al., Endothelial cells within embryonic skeletal muscles: a potential source of myogenic progenitors, Exp. Cell Res., 2004, 301:232-241.
Asakura et al., Myogenic specification of side population cells in skeletal muscle, (2002), J Cell Biol, 159:123-34.
Camargo et al., Single hematopoietic stem cells generate skeletal muscle through myeloid intermediates, (2003), Nat Med, 9:1520-7.
Cao et al., Muscle stem cells differentiate into haematopoietic lineages but retain myogenic potential, (2003), Nat Cell Biol, 5:640-6.
Corbel et al., Contribution of hematopoietic stem cells to skeletal muscle, (2003), Nat Med, 9:1528-32.
Ferrari et al., Failure to correct murine muscular dystrophy, (2001), Nature, 411:1014-5.
Fukada et al., Muscle regeneration by reconstitution with bone marrow or fetal liver cells from green fluorescent protein-gene transgenic mice, (2002), J Cell Sci, 115:1285-93.
Labarge et al., Biological progression from adult bone marrow to mononucleate muscle stem cell to multinucleate muscle fiber in response to injury, (2002), Cell, 111:589-601.
Polesskaya et al., Wnt signaling induces the myogenic specification of resident CD45+ adult stem cells during muscle regeneration, (2003), Cell, 113:841-52.
Qu-Petersen et al., Identification of a novel population of muscle stem cells in mice: potential for muscle regeneration, (2002), J Cell Biol, 157:851-64.
Wagers et al., Little evidence for developmental plasticity of adult hematopoietic stem cells, (2002), Science, 297:2256-9.

* cited by examiner

*Primary Examiner*—Celine X Qian
(74) *Attorney, Agent, or Firm*—Bozicevic, Field & Francis LLP; Pamela J. Sherwood

(57) ABSTRACT

Populations enriched for myogenic progenitors are obtained by selection on the basis of expression of specific cell surface markers. The muscle progenitor cells are characterized as being $CD45^-$ and $CD34^+$, and may further be characterized as lacking expression of Mac-1 (CD11b) and positive for expression of CXCR4 (CD184) and $\beta1$-integrin (CD29).

6 Claims, 12 Drawing Sheets
(10 of 12 Drawing Sheet(s) Filed in Color)

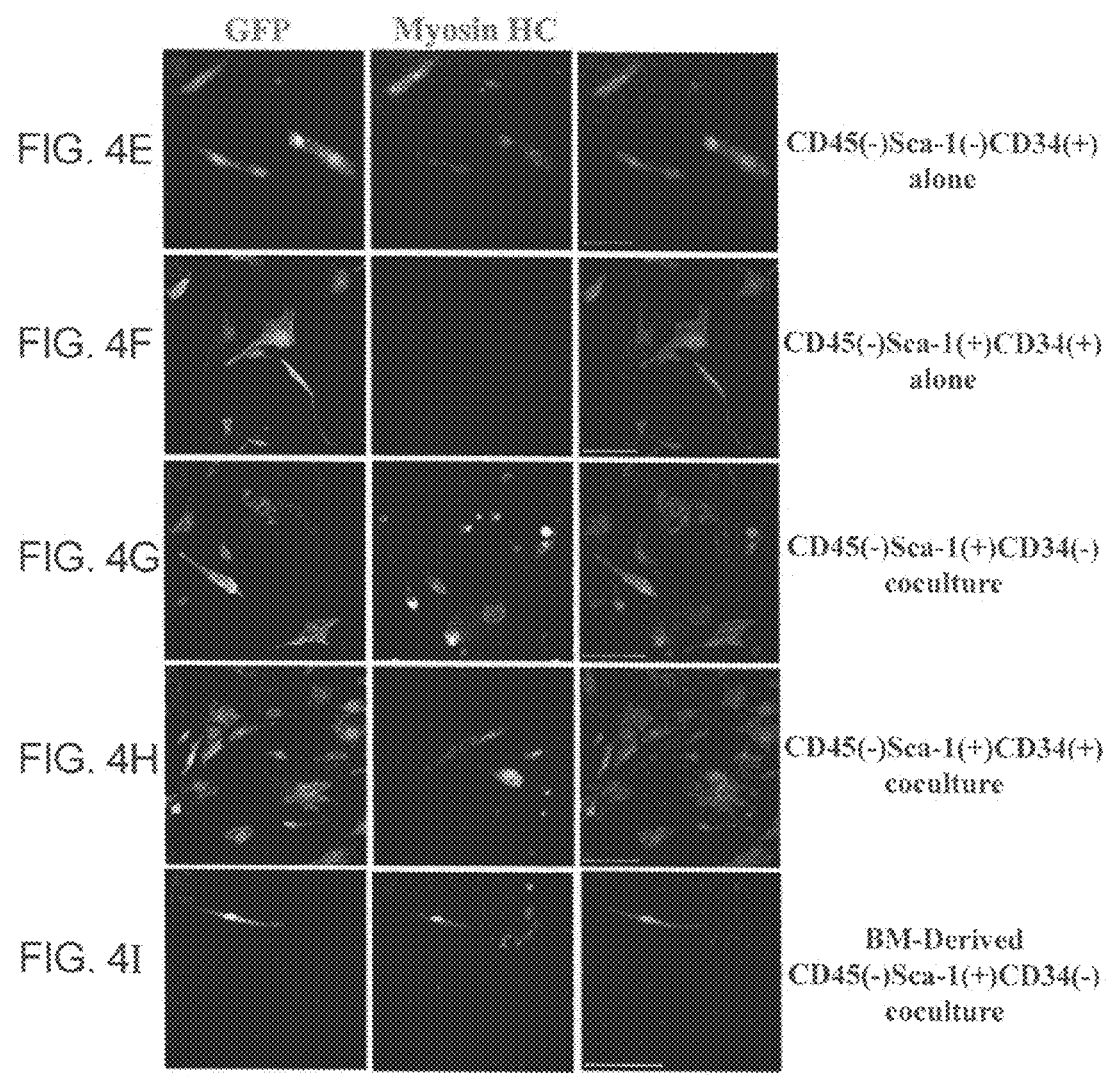

ISOLATION AND CHARACTERIZATION OF MUSCLE REGENERATING CELLS

BACKGROUND OF THE INVENTION

Stem cells have a capacity both for self-renewal and the generation of differentiated cell types. This pluripotentiality makes stem cells unique. In addition to studying the important normal function of stem cells in the regeneration of tissues, researchers have further sought to exploit the potential of in situ and/or exogenous stem cells for the treatment of a variety of disorders. While early, embryonic stem cells have generated considerable interest, the stem cells resident in adult tissues may also provide an important source of regenerative capacity.

These somatic, or adult, stem cells are undifferentiated cells that reside in differentiated tissues, and have the properties of self-renewal and generation of differentiated cell types. The differentiated cell types may include all or some of the specialized cells in the tissue. For example, hematopoietic stem cells give rise to all hematopoietic lineages, but do not seem to give rise to stromal and other cells found in the bone marrow. Sources of somatic stem cells include bone marrow, blood, the cornea and the retina of the eye, brain, skeletal muscle, dental pulp, liver, skin, the lining of the gastrointestinal tract, and pancreas. Adult stem cells are usually quite sparse. Often they are difficult to identify, isolate, and purify. Often, somatic stem cells are quiescent until stimulated by the appropriate growth signals.

Progenitor or precursor cells are similar to stem cells, but are usually considered to be distinct by virtue of lacking the capacity for self-renewal. Researchers often distinguish precursor/progenitor cells from stem cells in the following way: when a stem cell divides, one of the two new cells is often a stem cell capable of replicating itself again. In contrast, when a progenitor/precursor cell divides, it forms two specialized cells, neither of which is capable of replicating itself. Progenitor/precursor cells can replace cells that are damaged or dead, thus maintaining the integrity and functions of a tissue such as liver or brain.

Muscle tissue in adult vertebrates regenerates from reserve myoblasts called satellite cells. Satellite cells are distributed throughout muscle tissue and are mitotically quiescent in the absence of injury or disease. Following recovery from damage due to injury or disease or in response to stimuli for growth or hypertrophy, satellite cells reenter the cell cycle, proliferate and undergo differentiation into multinucleate myotubes, which form new muscle fiber. The myoblasts ultimately yield replacement muscle fibers or fuse into existing muscle fibers, thereby increasing fiber girth by the synthesis of contractile apparatus components. This process is illustrated, for example, by the nearly complete regeneration that occurs in mammals following induced muscle fiber degeneration or injury; the muscle progenitor cells proliferate and fuse together to regenerate muscle fibers.

Vertebrate muscles are thought to originate in the embryo from mesoderm-derived cells of the dorsal somites. During muscle development, some somite-derived myogenic progenitors do not differentiate into myofibers and instead are retained as muscle stem cells, or satellite cells, located beneath the basal lamina of muscle fibers. Satellite cells first appear in the limb muscles of mouse embryos between 16 and 18 days post conception (dpc). In neonatal mice, satellite cell nuclei comprise ~30% of myofiber-associated nuclei, but their number declines with age and only ~5% of myofiber nuclei in the muscles of adult mice represent satellite cells.

In injured adult muscle, satellite cell number and regenerative capacity remain nearly constant through multiple cycles of regeneration, suggesting that these cells may be capable of self-renewal, or that this population is maintained by self-renewing satellite cell precursors. Currently, satellite cells are defined both positionally, by their location beneath the basal lamina, and functionally, by their ability to undergo myogenic differentiation; however, potential heterogeneity in the function and/or origin of sublaminar myogenic cells may exist and has yet to be fully addressed.

In recent years, reports of adult skeletal muscle progenitors distinct from satellite cells have accumulated. For example, muscle-resident side population (muSP) cells, defined by their ability to exclude Hoechst 33342 and representing a population distinct from satellite cells, have been shown to contribute to myofibers when injected intramuscularly (McKinney-Freeman et al., 2002) or when co-cultured with myoblasts (Asakura et al. (2002) J Cell Biol 159,123-34), although muSP cells appear to lack myogenic activity when cultured alone.

Likewise, muscle-resident $CD45^+Sca-1^+$ cells fail to generate myogenic cells in vitro when cultured alone, but acquire myogenic potential when co-cultured with primary myoblasts or in response to muscle injury or activation of Wnt signaling by LiCl (Polesskaya et al. (2003) Cell 113, 841-52).

In addition, cells with high proliferative potential and the ability to differentiate into multiple cell types, including muscle, neural, endothelial, and hematopoietic lineages, have been isolated from muscle (Cao et al. (2003) Nat Cell Biol 5, 640-6; Qu-Petersen et al. (2002) J Cell Biol 157, 851-64). Finally, bone marrow cells recently have been suggested to contribute to myofibers when injected directly into injured muscle or intravenously into injured (Fukada et al. (2002) J Cell Sci 115, 1285-93) or mdx dystrophic animals (Ferrari et al. (2001) Nature 411, 1014-5). Even single hematopoietic stem cells (HSC), which reconstitute the entire hematopoietic system (Wagers et al. (2002) Science 297, 2256-9), also contribute at a low-level to skeletal myofibers following severe muscle injury (Camargo et al. (2003) Nat Med 9, 1520-7; Corbel et al. (2003) Nat Med 9, 1528-32).

However, whether contributions of BM cells to injured skeletal muscle proceed through the generation of muscle-resident satellite cell intermediates remains controversial. While some studies have reported the derivation of muscle-resident satellite cells from transplanted BM cells (LaBarge and Blau (2002) Cell 111, 589-601), others have suggested that donor-marker expressing myofibers arise via fusion of donor hematopoietic cells into existing host myofibers.

The ability to manipulate muscle regeneration is of great interest for clinical and research purposes. Characterization of stem and progenitor cells having myogenic potential is therefore of great interest.

SUMMARY OF THE INVENTION

Methods are provided for the separation and characterization of myogenic cells, which are progenitor cells having the ability to form muscle. This ability may be evidenced by various indicia, including expression of myogenic proteins; autonomous in vitro myogenic colony-forming capacity; myogenic capacity in co-culture with isolated muscle-resident myogenic cells; in vivo contribution to myofibers in injured muscle; and engraftment of the myofiber-associated compartment in vivo following intramuscular injection and subsequent maintenance of myogenic-colony forming capacity. Such myogenic progenitors are found to be associated with muscle fibers in vivo. Populations enriched for myogenic progenitors may be obtained by selection on the basis of expression of specific cell surface markers. The muscle progenitor cells are characterized as being CD45⁻ and CD34⁺, and may further be characterized as lacking expression of Mac-1 (CD11 b) and positive for expression of CXCR4 (CD184) and β1-integrin (CD29). In the mouse, the cells are negative for Sca-1.

A population of bone marrow derived cells, which are myofiber associated, and are also CD45⁻ and CD34⁺, are also provided. These cells can contribute to myofibers in vivo.

The progenitor cells are useful in transplantation, particularly for the regeneration of skeletal muscle, e.g. in the treatment of muscle disorders such as muscular dystrophies, myopathies, chanelopathies; following traumatic damage; and the like. The cells are also useful for experimental evaluation, and as a source of lineage and cell specific products, including mRNA species useful in identifying genes specifically expressed in these cells, and as targets for the discovery of factors or molecules that can affect them.

In vitro and in vivo systems are provided for the growth and analysis, including clonal analysis, of myogenic cells. Clonogenic assays may be performed in vitro in the presence or absence of additional co-cultured myofiber associated cells, where different cell populations vary in their ability to generate myogenic colonies.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 4A-4I. (A) Flow cytometric analysis of endogenous, uninjured myofiber-associated cells from an untransplanted GFP transgenic control mouse for expression of CD45, Sca-1, and CD34. Data are presented as contour plots of the indicated parameters, with the percent of cells that fall within each gate indicated. The leftmost plot is gated for live, GFP⁺ cells and shows gating (versus forward scatter (FSC)) for CD45⁺ or CD45⁻ subsets, with analysis of Sca-1 and CD34 expression of these sub-populations shown in the middle and right columns, respectively. (B) Statistical analysis of cell surface marker expression of endogenous myofiber-associated cells. Uninjured and 2d CDTX myofiber-associated preparations were analyzed by flow cytometry for expression of the indicated markers, and data are plotted as percentages of cells expressing those markers. (C) Relative frequency of cells capable of forming small, round, myogenic colonies among uninjured and 2d CDTX myofiber-associated populations, sorted by FACS from untransplanted GFP transgenic mice for the indicated markers. Data are plotted as the mean percent colony forming cells (CFC)+SD. (D) Relative frequency of myofiber-associated cells from untransplanted GFP transgenic mice capable of forming large, fibroblast-like colonies among uninjured and 2d CDTX myofiber-associated cell populations, sorted by FACS for the indicated markers. Data are plotted as the mean percent colony forming cells (CFC)+SD. (E-I) Representative micrographs showing in vitro myogenic differentiation to MHC-expressing myocytes of cells isolated from control GFP transgenic animals (E-H) or BM-transplanted animals (I) by FACS for the indicated markers. CD45⁻ Sca-1⁺ (E) or CD45⁻ Sca-1⁺ (F) myofiber-associated cells were cultured alone then analyzed by fluorescence microscopy for expression of MHC. CD45⁻ Sca-1⁺ CD34⁻ (G), CD45⁻ Sca-1⁺ CD34⁺ (H), or BM-derived CD45⁻ Sca-1⁺ CD34⁻ (I) cells were co-cultured with HcRed-expressing myofiber-associated cells from an HcRed transgenic animal and then analyzed for expression of MHC. Left column, GFP, middle column, MHC; right column, electronically merged image with MHC shown in red and GFP shown in green; scalebar=100 μm.

DESCRIPTION OF THE SPECIFIC EMBODIMENTS

Figure 1:
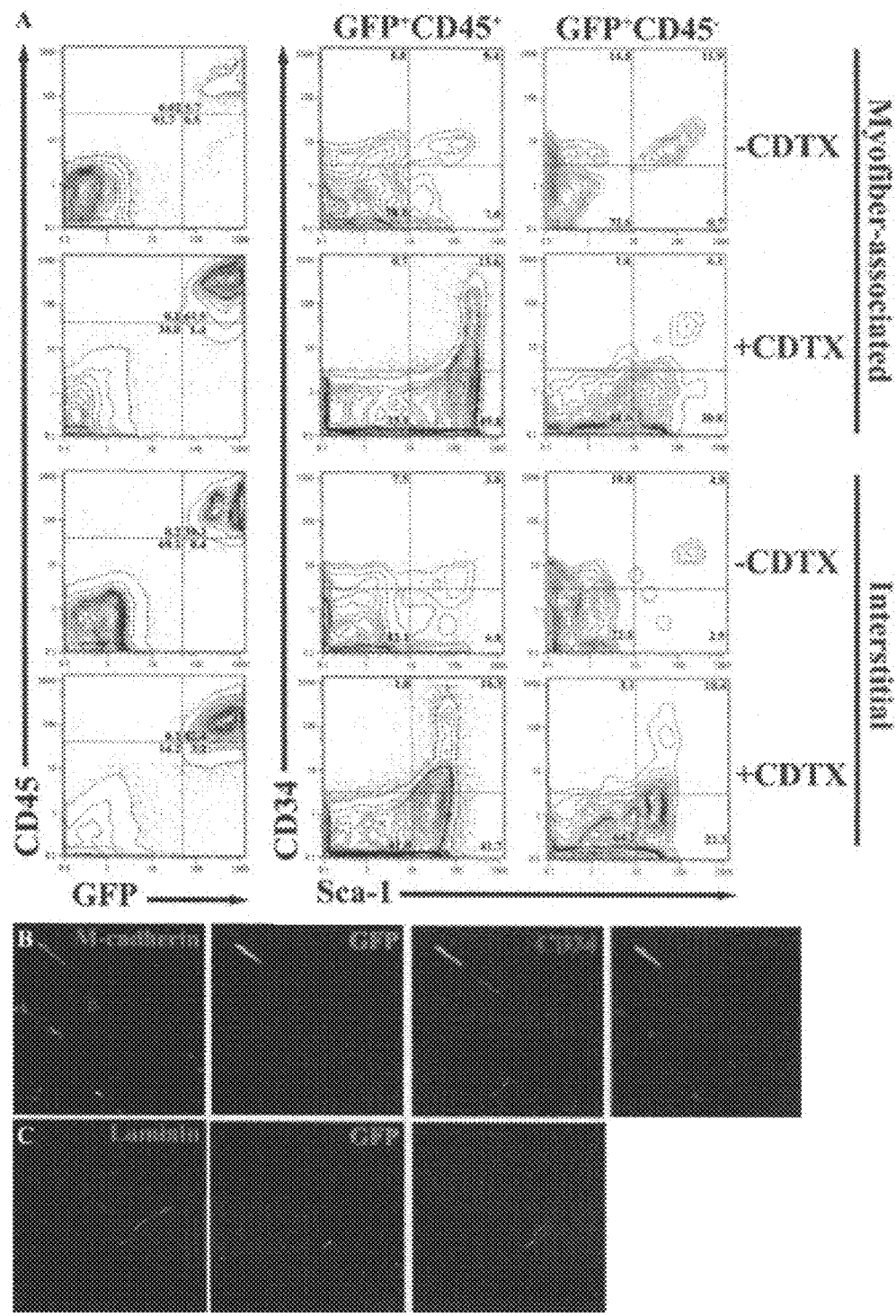
FIGS. 1A-1C. (A) Flow cytometric analysis of muscle mononuclear cell populations in injured or uninjured muscle of BM-transplanted mice. Uninjured (−CDTX) or 2d CDTX-injured (+CDTX) muscles from animals previously transplanted with GFP⁺ BM cells were dissociated, and myofiber-associated or interstitial cells analyzed for expression of GFP, CD45, Sca-1, and CD34, as indicated. Data are presented as contour plots of the indicated parameters, with the percent of cells that fall within each gate indicated. The leftmost plot is gated for live cells and shows gating for GFP⁺ CD45⁻ or GFP⁺ CD45⁺ subsets, with analysis of Sca-1 and CD34 expression of these sub-populations shown in the middle and right columns, respectively. (B, C) Representative confocal micrographs showing immunofluorescence analysis of frozen sections of injured TS muscles from a BM-transplanted animal. Muscles were injured ~8 weeks prior to harvesting. Sections were analyzed for (B) co-localization of M-cadherin, CD34 and GFP or (C) sublaminar localization of GFP+ cells. First column, M-cadherin (B) or laminin (C); second column, GFP; third column, CD34 (B) or electronically merged image with laminin shown in red, GFP in green and Hoechst 33342 staining of nuclei in blue (C); and fourth column, electronically merged image with M-cadherin shown in red, GFP in green and CD34 in blue (B); scalebar=100 μm.

Methods are provided for the separation and characterization of myogenic progenitor cells; and compositions of cells enriched for myogenic progenitors are provided. Use of a procedure that separates muscle-resident cells into a myofiber-associated compartment highly enriched for satellite cells, and a separate interstitial cell preparation, has allowed direct analysis of these different cells' myogenic potential. The ability to sort these distinct populations freshly from muscle facilitates determination of cell lineage relationships in the differentiation of muscle stem cells and progenitors as well as the determination of the signaling pathways and gene expression dynamics important for maintaining muscle-resident cell populations.

It is shown herein that only endogenous muscle resident cells are able to fulfill various criteria for a myogenic progenitor, including the ability to generate autonomous in vitro myogenic colonies; in vivo contribution to myofibers in injured muscle; and engraftment of the myofiber-associated compartment in vivo following intramuscular injection and subsequent maintenance of myogenic-colony forming capacity. Cells derived from circulating bone marrow or hematopoietic stem cells were able to contribute to muscle only in certain conditions, e.g. in a co-culture with myofiber associated cells, by fusion with existing myofibers, etc.

The subject cells are useful in transplantation, particularly for the regeneration of skeletal muscle, e.g. in the treatment of muscle disorders such as muscular dystrophies, myopathies, chanelopathies; following traumatic damage; and the like. The cells are also useful for experimental evaluation, and as a source of lineage and cell specific products, including mRNA species useful in identifying genes specifically expressed in these cells, and as targets for the discovery of factors or molecules that can affect them.

The endogenous myofiber associated cells having progenitor cell activity were found to be CD45− and CD34+. A more highly enriched population was obtained by additionally selecting for Mac-1⁻ CXCR4⁺ and β1-integrin⁺ cells. These cells also lack expression of Sca-1, which marker is useful for selection with mouse cells.

The myofiber-associated cell compartment contains not only these fully myogenic cells but also several distinct cell populations with limited or no myogenic capacity. These include CD45⁻CD34⁺ Sca-1⁺ cells, which express vimentin and form fibroblast-like colonies, and CD45⁺ cells, most of which are Mac-1⁺ myeloid lineage cells derived from BM HSC that possess no myogenic activity in vitro. Under certain experimental conditions, as described in the Examples, a population of cells derived from bone marrow (BM) is also localized to the same anatomical compartment as muscle satellite cells. These BM derived cells had a phenotype superficially similar to the myogenic progenitor cells, i.e. CD45⁻ CD34⁺ Sca-1⁻ and can generate myosin heavy chain (MHC)-expressing cells when co-cultured with endogenous myogenic cells, but not when cultured alone. This co-culture-induced myogenic activity does not derive from HSC or their progeny, as HSC-derived muscle-resident cells do not display myogenic activity either alone or in co-culture experiments. The induction of expression of muscle-specific markers by BM-derived cells in vitro occurs in the absence of cell fusion, suggesting that limited myogenic differentiation or conversion of BM cells may occur through the process of transplantation, muscle homing, engraftment in the myofiber-associated fraction and/or subsequent isolation and culture. The BM derived cells do not appear to have an intrinsic ability to independently differentiate into muscle cells; however, these cells did contribute to myofiber formation in vivo through cell fusion events.

The subject cells may be used for reconstitution of muscle function in a recipient. Allogeneic cells may be used for progenitor cell isolation and subsequent transplantation, for example where the disease conditions result from genetic defects in muscle cell function. Where the muscle dysfunction arises from conditions such as trauma, the subject cells may be isolated from autologous tissue, and used to regenerate function. Autologous cells may also be genetically modified, in order to correct disease conditions results from genetic defects.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "an", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

Myogenic Progenitors. As used herein, the term myogenic progenitor is used to refer to cells that can form muscle. For many purposes, the primary requirement is an ability to contribute to myofiber formation in vivo, e.g. in injured muscle. As shown herein, a population of endogenous myofiber associated cells have this capability. Under some circumstances a bone marrow derived cell population also has this capability, however because this cell lacks some other capabilities, it will generally be referred to herein as a "BM derived myogenic cell".

Additional criteria for myogenicity include the expression of myogenic proteins, which include the intermediate filament protein desmin, myogenic transcription factors MyoD, Myf-5 and Pax-7.

Under myogenic conditions in vitro, myogenic progenitor cells will generally autonomously give rise to myogenic colonies. Myogenic conditions may include the presence of a substrate, such as collagen or laminin, where medium may include bFGF. The growth conditions may be changed to fusion conditions in the absence of bFGF for myofiber formation. BM derived myogenic cells, lacking autonomous CFC, may give rise to myogenic colonies when co-cultured with myogenic precursors.

The stem/progenitor capability of myogenic progenitors is evidenced by the ability to engraft and repopulate the myofiber-associated compartment in vivo following intramuscular injection, and subsequent maintenance of myogenic-colony forming capacity.

The term muscle cell as used herein refers to any cell that contributes to muscle tissue. Myoblasts, satellite cells, myotubes, and myofibril tissues are all included in the term "muscle cells". Muscle cell effects may be induced within skeletal, cardiac and smooth muscles, particularly with skeletal muscle.

Activation of satellite cells in muscle tissue can result in the production of new muscle cells in the patient. Muscle regeneration as used herein refers to the process by which new muscle fibers form from muscle progenitor cells. A therapeutic composition will usually confer an increase in the number of new fibers by at least 1%, more preferably by at least 20%, and most preferably by at least 50%. The growth of muscle may occur by the increase in the fiber size and/or by increasing the number of fibers. The growth of muscle may be measured by an increase in wet weight, an increase in protein content, an increase in the number of muscle fibers, an increase in muscle fiber diameter; etc. An increase in growth of a muscle fiber can be defined as an increase in the diameter where the diameter is defined as the minor axis of ellipsis of the cross section.

Muscle regeneration may also be monitored by the mitotic index of muscle. For example, cells may be exposed to a labeling agent for a time equivalent to two doubling times. The mitotic index is the fraction of cells in the culture which have labeled nuclei when grown in the presence of a tracer which only incorporates during S phase (i.e., BrdU) and the doubling time is defined as the average S time required for the number of cells in the culture to increase by a factor of two. Productive muscle regeneration may be also monitored by an increase in muscle strength and agility.

Muscle regeneration may also be measured by quantitation of myogenesis, i.e. fusion of myoblasts to yield myotubes. An effect on myogenesis results in an increase in the fusion of myoblasts and the enablement of the muscle differentiation program. For example, the myogenesis may be measured by the fraction of nuclei present in multinucleated cells in relative to the total number of nuclei present. Myogenesis may also be determined by assaying the number of nuclei per area in myotubes or by measurement of the levels of muscle specific protein by Western analysis.

The survival of muscle fibers may refer to the prevention of loss of muscle fibers as evidenced by necrosis or apoptosis or the prevention of other mechanisms of muscle fiber loss.

Mucles can be lost from injury, atrophy, and the like, where atrophy of muscle refers to a significant loss in muscle fiber girth.

Positive and negative staining. The subject myogenic progenitor cells are characterized by their expression of cell surface markers. While it is commonplace in the art to refer to cells as "positive" or "negative" for a particular marker, actual expression levels are a quantitative trait. The number of molecules on the cell surface can vary by several logs, yet still be characterized as "positive". It is also understood by those of skill in the art that a cell which is negative for staining, i.e. the level of binding of a marker specific reagent is not detectably different from a control, e.g. an isotype matched control; may express minor amounts of the marker. Characterization of the level of staining permits subtle distinctions between cell populations.

The staining intensity of cells can be monitored by flow cytometry, where lasers detect the quantitative levels of fluorochrome (which is proportional to the amount of cell surface marker bound by specific reagents, e.g. antibodies). Flow cytometry, or FACS, can also be used to separate cell populations based on the intensity of binding to a specific reagent, as well as other parameters such as cell size and light scatter. Although the absolute level of staining may differ with a particular fluorochrome and reagent preparation, the data can be normalized to a control.

In order to normalize the distribution to a control, each cell is recorded as a data point having a particular intensity of staining. These data points may be displayed according to a log scale, where the unit of measure is arbitrary staining intensity. In one example, the brightest stained cells in a sample can be as much as 4 logs more intense than unstained cells. When displayed in this manner, it is clear that the cells falling in the highest log of staining intensity are bright, while those in the lowest intensity are negative. The "low" positively stained cells have a level of staining above the brightness of an isotype matched control, but it is not as intense as the most brightly staining cells normally found in the population. Low positive cells may have unique properties that differ from the negative and brightly stained positive cells of the sample. An alternative control may utilize a substrate having a defined density of marker on its surface, for example a fabricated bead or cell line, which provides the positive control for intensity.

Sources of Progenitor Cells. Ex vivo and in vitro cell populations useful as a source of cells may include fresh or frozen muscle fiber cell populations, usually skeletal muscle, obtained from embryonic, fetal, pediatric or adult tissue. The methods can include further enrichment or purification procedures or steps for cell isolation by positive selection for other cell specific markers. The progenitor cells may be obtained from any mammalian species, e.g. human, equine, bovine, porcine, canine, feline, rodent, e.g. mice, rats, hamster, primate, etc.

Markers. The markers for selection of myogenic progenitors and/or BM derived myogenic cells will vary with the specific cells. As described above, a number of well-known markers can be used for positive selection and negative selection. Useful markers for positive selection may include, without limitation, one, two or more of: CD34, CXCR4, c-met (HGF-receptor), and beta 1-integrin. Useful markers for negative selection may include, without limitation, one, two or more of: CD45, Sca-1, Mac-1, B220, CD3, Gr-1, Thy-1, c-Kit, CD13, CD44, CD71, CD105, Flk-1, Flk-2, alpha1-integrin, and alpha6-integrin.

Marker combinations of interest include, without limitation, CD45, CD34, Mac-1, CXCR4 and β1-integrin.

Specific Binding Member. The term "specific binding member" or "binding member" as used herein refers to a member of a specific binding pair, i.e. two molecules, usually two different molecules, where one of the molecules (i.e., first specific binding member) through chemical or physical means specifically binds to the other molecule (i.e., second specific binding member). The complementary members of a specific binding pair are sometimes referred to as a ligand and receptor; or receptor and counter-receptor. Such specific binding members are useful in positive and negative selection methods. Specific binding pairs of interest include carbohydrates and lectins; complementary nucleotide sequences; peptide ligands and receptor; effector and receptor molecules; hormones and hormone binding protein; enzyme cofactors and enzymes; enzyme inhibitors and enzymes; antibodies and antigens; etc. The specific binding pairs may include analogs, derivatives and fragments of the original specific binding member. For example, a receptor and ligand pair may include peptide fragments, chemically synthesized peptidomimetics, labeled protein, derivatized protein, etc.

Especially useful reagents are antibodies specific for markers present on the desired cells (for positive selection) and undesired cells (for negative selection). Whole antibodies may be used, or fragments, e.g. Fab, $F(ab')_2$, light or heavy chain fragments, etc. Such selection antibodies may be polyclonal or monoclonal and are generally commercially available or alternatively, readily produced by techniques known to those skilled in the art. Antibodies selected for use will have a low level of non-specific staining and will usually have an affinity of at least about 100 μM for the antigen.

In one embodiment of the invention, antibodies for selection are coupled to a label. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red, cy7, cy5. Frequently each antibody is labeled with a different fluorochrome, to permit independent sorting for each marker. The exact method for coupling to a label is not critical to the practice of the invention, and a number of alternatives are known in the art. Direct coupling attaches the antibodies to the label. Indirect coupling can be accomplished by several methods. The antibodies may be coupled to one member of a high affinity binding system, e.g. biotin, and the particles attached to the other member, e.g. avidin. One may also use second stage antibodies that recognize species-specific epitopes of the antibodies, e.g. anti-mouse Ig, anti-rat Ig, etc. Indirect coupling methods allow the use of a single labeled entity, e.g. antibody, avidin, etc., with a variety of separation antibodies.

Enrichment Methods

The subject myogenic cells are separated from a complex mixture of cells by techniques that enrich for cells having the characteristics as described. For example, a muscle sample may initially be prepared by dissociation of myofibers. From this population, cells may be selected for expression of one or more of CD34, CXCR4, c-met (HGF-receptor), and beta 1-integrin; and negatively selected for one or more of: CD45, Sca-1, Mac-1, B220, CD3, Gr-1, Thy-1, c-Kit, CD13, CD44, CD71, CD105, Flk-1, Flk-2, alpha1-integrin, and alpha6-integrin.

Dissociation of muscle usually includes digestion with a suitable protease, e.g. collagenase, dispase, etc., followed by trituration until dissociated into myofiber fragments. Fragments are then washed and further enzymatically dissociated to generate a population of myofiber associated cells. An appropriate solution is used for dispersion or suspension. Such solution will generally be a balanced salt solution, e.g. normal saline, PBS, Hanks balanced salt solution, etc., supplemented with fetal calf serum or other naturally occurring factors, in conjunction with an acceptable buffer at low concentration, generally from 5-25 mM. Convenient buffers include HEPES, phosphate buffers, lactate buffers, etc.

Separation of the subject cell population will then use affinity separation to provide a substantially pure population. Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (propidium iodide, 7-AAD). Any technique may be employed which is not unduly detrimental to the viability of the selected cells.

The affinity reagents may be specific receptors or ligands for the cell surface molecules indicated above. The details of the preparation of antibodies and their suitability for use as specific binding members are well known to those skilled in the art. Of particular interest is the use of antibodies as affinity reagents.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium which maintains the viability of the cells. A preferred medium is phosphate buffered saline containing from 0.1 to 0.5% BSA. Various media are commercially available and may be used according to the nature of the cells, including Dulbeccos Modified Eagle Medium (dMEM), Hank's Basic Salt Solution (HBSS), Dulbeccos phosphate buffered saline (dPBS), RPMI, Iscoves medium, PBS with 5 mM EDTA, etc., frequently supplemented with fetal calf serum, BSA, HSA, etc.

The labeled cells are then separated as to the phenotype described above. The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscoves medium, etc., frequently supplemented with fetal calf serum.

Compositions highly enriched for muscle engrafting activity are achieved in this manner. The subject population will be at or about 50% or more of the cell composition, and usually at or about 90% or more of the cell composition, and may be as much as about 95% or more of the live cell population. The enriched cell population may be used immediately, or may be frozen at liquid nitrogen temperatures and stored for long periods of time, being thawed and capable of being reused. The cells will usually be stored in 10% DMSO, 50% FCS, 40% RPMI 1640 medium. Once thawed, the cells may be expanded by use of growth factors and/or feeder cells for proliferation and differentiation.

The compositions thus obtained have a variety of uses in clinical therapy, research, development, and commercial purposes. For therapeutic purposes, for example, myocytes and their precursors may be administered to enhance tissue maintenance or repair of muscle for any perceived need, such as an inborn error in metabolic function, the effect of a disease condition, or the result of significant trauma.

To determine the suitability of cell compositions for therapeutic administration, the cells can first be tested in a suitable animal model. At one level, cells are assessed for their ability to survive and generate the desired phenotype in vivo. Cell compositions may be administered to immunodeficient animals (such as nude mice, or animals rendered immunodeficient chemically or by irradiation). Tissues are harvested after a period of regrowth, and assessed as to whether the administered cells or progeny thereof are still present.

This can be performed by administering cells that express a detectable label (such as green fluorescent protein, or β-galactosidase); that have been prelabeled (for example, with BrdU or [$^3$H] thymidine), or by subsequent detection of a constitutive cell marker (for example, using human-specific antibody). The presence and phenotype of the administered cells can be assessed by immunohistochemistry or ELISA using human-specific antibody, or by RT-PCR analysis using primers and hybridization conditions that cause amplification to be specific for human polynucleotides, according to published sequence data.

Where the differentiating cells are cells of the myocyte lineage, suitability can also be determined in an animal model by assessing the degree of muscle regeneration that ensues from treatment with the differentiating cells of the invention. A number of animal models are available for such testing. For example, muscle can be injured as described in the Examples. Injured sites are treated with cell preparations of this invention, and the muscle tissue is examined by histology for the presence of the cells in the damaged area.

Cells may be genetically altered in order to introduce genes useful in the differentiated cell, e.g. repair of a genetic defect in an individual, selectable marker, etc. Cells may be genetically altering by transfection or transduction with a suitable vector, homologous recombination, or other appropriate technique, so that they express a gene of interest. In one embodiment, cells are transfected with genes encoding dystrophin. In other embodiments, a selectable marker is introduced, to provide for greater purity of the desired cell. Cells may be genetically altered using vector containing supernatants over a 8-16 h period, and then exchanged into growth medium for 1-2 days. Genetically altered cells are selected using a drug selection agent such as puromycin, G418, or blasticidin, and then recultured. Genetically modified cells can also be selected for a detectable marker, e.g. GFP, etc., by cell sorting methods known in the art.

Many vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. Retrovirus based vectors have been shown to be particularly useful when the target cells are progenitor cells. For example, see Schwarzenberger et al. (1996) Blood 87:472-478; Nolta et al. (1996) P. N. A. S. 93:2414-2419; and Maze et al. (1996) P. N. A. S. 93:206-210.

Combinations of retroviruses and an appropriate packaging line may be used, where the capsid proteins will be functional for infecting the target cells. Usually, the cells and virus will be incubated for at least about 24 hours in the culture medium. The cells are then allowed to grow in the culture medium for short intervals in some applications, e.g. 24-73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line.

Lentiviral vectors such as those based on HIV or FIV gag sequences can be used to transfect non-dividing cells, such as the resting phase of human stem cells (see Uchida et al. (1998) *P.N.A.S.* 95(20):11939-44).

The host cell specificity of the retrovirus is determined by the envelope protein, env (p120). The envelope protein is provided by the packaging cell line. Envelope proteins are of at least three types, ecotropic, amphotropic and xenotropic. Retroviruses packaged with ecotropic envelope protein, e.g. MMLV, are capable of infecting most murine and rat cell types. Ecotropic packaging cell lines include BOSC23 (Pear et al. (1993) P. N. A. S. 90:8392-8396). Retroviruses bearing amphotropic envelope protein, e.g. 4070A (Danos et al, supra.), are capable of infecting most mammalian cell types, including human, dog and mouse. Amphotropic packaging cell lines include PA12 (Miller et al. (1985) *Mol. Cell. Biol.* 5:431-437); PA317 (Miller et al. (1986) *Mol. Cell. Biol.* 6:2895-2902) GRIP (Danos et al. (1988) *PNAS* 85:6460-6464). Retroviruses packaged with xenotropic envelope protein, e.g. AKR env, are capable of infecting most mammalian cell types, except murine cells.

The vectors may include genes that must later be removed, e.g. using a recombinase system such as Cre/Lox, or the cells that express them destroyed, e.g. by including genes that allow selective toxicity such as herpesvirus TK, bcl-xs, etc.

Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in different cell types.

Therapeutic Methods

The myogenic cells may be used for tissue reconstitution or regeneration in a human patient or other subject in need of such treatment. The cells are administered in a manner that permits them to graft or migrate to the intended tissue site and reconstitute or regenerate the functionally deficient area.

The differentiating cells may be administered in any physiologically acceptable excipient, where the cells may find an appropriate site for regeneration and differentiation. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FCS, 40% RPMI 1640 medium. Once thawed, the cells may be expanded by use of growth factors and/or feeder cells associated with progenitor cell proliferation and differentiation.

The cells of this invention can be supplied in the form of a pharmaceutical composition, comprising an isotonic excipient prepared under sufficiently sterile conditions for human administration. Choice of the cellular excipient and any accompanying elements of the composition will be adapted in accordance with the route and device used for administration. The composition may also comprise or be accompanied with one or more other ingredients that facilitate the engraftment or functional mobilization of the cells. Suitable ingredients include matrix proteins that support or promote adhesion of the cells.

The subject methods are useful for both prophylactic and therapeutic purposes. Thus, as used herein, the term "treating" is used to refer to both prevention of disease, and treatment of a pre-existing condition. The treatment of ongoing disease, to stabilize or improve the clinical symptoms of the patient, is a particularly important benefit provided by the present invention. Such treatment is desirably performed prior to loss of function in the affected tissues; consequently, the prophylactic therapeutic benefits provided by the invention are also important. Evidence of therapeutic effect may be any diminution in the severity of disease. The therapeutic effect can be measured in terms of clinical outcome or can be determined by immunological or biochemical tests.

The dosage of the therapeutic formulation will vary widely, depending upon the nature of the condition, the frequency of administration, the manner of administration, the clearance of the agent from the host, and the like. The initial dose can be larger, followed by smaller maintenance doses. The dose can be administered as infrequently as weekly or biweekly, or more often fractionated into smaller doses and administered daily, semi-weekly, or otherwise as needed to maintain an effective dosage level.

Disease Conditions

Diseases of interest for treatment with the subject cells, particularly allogeneic cells and/or genetically modified autologous cells, include muscular dystrophies. Duchenne dystrophy is an X-linked recessive disorder characterized by progressive proximal muscle weakness with destruction and regeneration of muscle fibers and replacement by connective tissue. Duchenne dystrophy is caused by a mutation at the Xp21 locus, which results in the absence of dystrophin, a protein found inside the muscle cell membrane. It affects 1 in 3000 live male births. Symptoms typically start in boys aged 3 to 7 yr. Progression is steady, and limb flexion contractures and scoliosis develop. Firm pseudohypertrophy (fatty and fibrous replacement of certain enlarged muscle groups, notably the calves) develops. Most patients are confined to a wheelchair by age 10 or 12 and die of respiratory complications by age 20.

Becker muscular dystrophy is a less severe variant, also due to a mutation at the Xp21 locus. Dystrophin is reduced in quantity or in molecular weight. Patients usually remain ambulatory, and most survive into their 30s and 40s.

Among the non-dystrophic myopathies are congenital and metabolic myopathies, including glycogen storage diseases and mitochondrial myopathies. Congenital myopathies are a heterogeneous group of disorders that cause hypotonia in infancy or weakness and delayed motor milestones later in childhood. An autosomal dominant form of nemaline myopathy is linked to chromosome 1 (tropomyosin gene), and a recessive form to chromosome 2. Other forms are caused by mutations in the gene for the ryanodine receptor (the calcium release channel of the sarcoplasmic reticulum) on chromosome 19q. Skeletal abnormalities and dysmorphic features are common. Diagnosis is made by histochemical and electron microscopic examination of a muscle sample to identify specific morphologic changes.

Mitochondrial myopathies range from mild, slowly progressive weakness of the extraocular muscles to severe, fatal infantile myopathies and multisystem encephalomyopathies. Some syndromes have been defined, with some overlap between them. Established syndromes affecting muscle include progressive external ophthalmoplegia, the Kearns-Sayre syndrome (with ophthalmoplegia, pigmentary retinopathy, cardiac conduction defects, cerebellar ataxia, and sensorineural deafness), the MELAS syndrome (mitochondrial encephalomyopathy, lactic acidosis, and stroke-like episodes), the MERFF syndrome (myoclonic epilepsy and ragged red fibers), limb-girdle distribution weakness, and infantile myopathy (benign or severe and fatal). Muscle biopsy specimens stained with modified Gomori's trichrome stain show ragged red fibers due to excessive accumulation of mitochondria. Biochemical defects in substrate transport and utilization, the Krebs cycle, oxidative phosphorylation, or the respiratory chain are detectable. Numerous mitochondrial DNA point mutations and deletions have been described, transmitted in a maternal, nonmendelian inheritance pattern. Mutations in nuclear-encoded mitochondrial enzymes occur.

Glycogen storage diseases of muscle are a group of rare autosomal recessive diseases characterized by abnormal accumulation of glycogen in skeletal muscle due to a specific biochemical defect in carbohydrate metabolism. These diseases can be mild or severe. In a severe form, acid maltase deficiency (Pompe's disease), in which 1,4-glucosidase is absent, is evident in the first year of life and is fatal by age 2. Glycogen accumulates in the heart, liver, muscles, and nerves. In a less severe form, this deficiency may produce proximal limb weakness and diaphragm involvement causing hypoventilation in adults. Myotonic discharges in paraspinal muscles are commonly seen on electromyogram, but myotonia does not occur clinically. Other enzyme deficiencies cause painful cramps after exercise, followed by myoglobinuria. The diagnosis is supported by an ischemic exercise test without an appropriate rise in serum lactate and is confirmed by demonstrating a specific enzyme abnormality.

Channelopathies are neuromuscular disorders with functional abnormalities due to disturbance of the membrane conduction system, resulting from mutations affecting ion channels. Myotonic disorders are characterized by abnormally slow relaxation after voluntary muscle contraction due to a muscle membrane abnormality.

Myotonic dystrophy (Steinert's disease) is an autosomal dominant multisystem disorder characterized by dystrophic muscle weakness and myotonia. The molecular defect is an expanded trinucleotide (CTG) repeat in the 3' untranslated region of the myotonin-protein kinase gene on chromosome 19q. Symptoms can occur at any age, and the range of clinical severity is broad. Myotonia is prominent in the hand muscles, and ptosis is common even in mild cases. In severe cases, marked peripheral muscular weakness occurs, often with cataracts, premature balding, hatchet facies, cardiac arrhythmias, testicular atrophy, and endocrine abnormalities. Mental retardation is common. Severely affected persons die by their early 50s.

Myotonia congenita (Thomsen's disease) is a rare autosomal dominant myotonia that usually begins in infancy. In several families, the disorder has been linked to a region on chromosome 7 containing a skeletal muscle chloride channel gene. Painless muscle stiffness is most troublesome in the hands, legs, and eyelids and improves with exercise. Weakness is usually minimal. Muscles may become hypertrophied. Diagnosis is usually established by the characteristic physical appearance, by inability to release the handgrip rapidly, and by sustained muscle contraction after direct muscle percussion.

Familial periodic paralysis is a group of rare autosomal dominant disorders characterized by episodes of flaccid paralysis with loss of deep tendon reflexes and failure of muscle to respond to electrical stimulation. The hypokalemic form is due to genetic mutation in the dihydropyridine receptor-associated calcium channel gene on chromosome 1q. The hyperkalemic form is due to mutations in the gene on chromosome 17q that encodes a subunit of the skeletal muscle sodium channel (SCN4A).

Libraries

The cells of this invention can be used to prepare a cDNA library relatively uncontaminated with cDNA preferentially expressed in cells from other lineages. For example, myogenic progenitors are collected by centrifugation at 1000 rpm for 5 min, and then mRNA is prepared from the pellet by standard techniques (Sambrook et al., supra). After reverse transcribing into cDNA, the preparation can be subtracted with cDNA from other progenitor cells, or end-stage cells from the myocyte or any other developmental pathway.

The cells of this invention can also be used to prepare antibodies that are specific for markers of myocytes and their precursors. Polyclonal antibodies can be prepared by injecting a vertebrate animal with cells of this invention in an immunogenic form. Production of monoclonal antibodies is described in standard references. Specific antibody molecules can also be produced by contacting a library of immunocompetent cells or viral particles with the target antigen, and growing out positively selected clones. See Marks et al., New Eng. J. Med. 335:730, 1996, and McGuiness et al., Nature Biotechnol. 14:1449, 1996. A further alternative is reassembly of random DNA fragments into antibody encoding regions, as described in EP patent application 1,094,108 A.

The antibodies in turn can be used to identify or rescue cells of a desired phenotype from a mixed cell population, for purposes such as costaining during immunodiagnosis using tissue samples, and isolating precursor cells from terminally differentiated myocytes and cells of other lineages.

Of particular interest is the examination of gene expression in the myogenic cells of the invention. The expressed set of genes may be compared against other subsets of cells, against other stem or progenitor cells, against adult muscle tissue, and the like, as known in the art. Any suitable qualitative or quantitative methods known in the art for detecting specific mRNAs can be used. mRNA can be detected by, for example, hybridization to a microarray, in situ hybridization in tissue sections, by reverse transcriptase-PCR, or in Northern blots containing poly A+ mRNA. One of skill in the art can readily use these methods to determine differences in the size or amount of mRNA transcripts between two samples.

Any suitable method for detecting and comparing mRNA expression levels in a sample can be used in connection with the methods of the invention. For example, mRNA expression levels in a sample can be determined by generation of a library of expressed sequence tags (ESTs) from a sample. Enumeration of the relative representation of ESTs within the library can be used to approximate the relative representation of a gene transcript within the starting sample. The results of EST analysis of a test sample can then be compared to EST analysis of a reference sample to determine the relative expression levels of a selected polynucleotide, particularly a polynucleotide corresponding to one or more of the differentially expressed genes described herein.

Alternatively, gene expression in a test sample can be performed using serial analysis of gene expression (SAGE)

methodology (Velculescu et al., *Science* (1995) 270:484). In short, SAGE involves the isolation of short unique sequence tags from a specific location within each transcript. The sequence tags are concatenated, cloned, and sequenced. The frequency of particular transcripts within the starting sample is reflected by the number of times the associated sequence tag is encountered with the sequence population.

Gene expression in a test sample can also be analyzed using differential display (DD) methodology. In DD, fragments defined by specific sequence delimiters (e.g., restriction enzyme sites) are used as unique identifiers of genes, coupled with information about fragment length or fragment location within the expressed gene. The relative representation of an expressed gene with a sample can then be estimated based on the relative representation of the fragment associated with that gene within the pool of all possible fragments. Methods and compositions for carrying out DD are well known in the art, see, e.g., U.S. Pat. No. 5,776,683; and U.S. Pat. No. 5,807,680.

Alternatively, gene expression in a sample using hybridization analysis, which is based on the specificity of nucleotide interactions. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample. Hybridization analysis can be designed to allow for concurrent screening of the relative expression of hundreds to thousands of genes by using, for example, array-based technologies having high density formats, including filters, microscope slides, or microchips, or solution-based technologies that use spectroscopic analysis (e.g., mass spectrometry). One exemplary use of arrays in the diagnostic methods of the invention is described below in more detail.

Hybridization to arrays may be performed, where the arrays can be produced according to any suitable methods known in the art. For example, methods of producing large arrays of oligonucleotides are described in U.S. Pat. No. 5,134,854, and U.S. Pat. No. 5,445,934 using light-directed synthesis techniques. Using a computer controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in PCT published application no. WO 95/35505.

Methods for collection of data from hybridization of samples with an array are also well known in the art. For example, the polynucleotides of the cell samples can be generated using a detectable fluorescent label, and hybridization of the polynucleotides in the samples detected by scanning the microarrays for the presence of the detectable label. Methods and devices for detecting fluorescently marked targets on devices are known in the art. Generally, such detection devices include a microscope and light source for directing light at a substrate. A photon counter detects fluorescence from the substrate, while an x-y translation stage varies the location of the substrate. A confocal detection device that can be used in the subject methods is described in U.S. Pat. No. 5,631,734. A scanning laser microscope is described in Shalon et al., *Genome Res.* (1996) 6:639. A scan, using the appropriate excitation line, is performed for each fluorophore used. The digital images generated from the scan are then combined for subsequent analysis. For any particular array element, the ratio of the fluorescent signal from one sample is compared to the fluorescent signal from another sample, and the relative signal intensity determined.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e. data deviating from a predetermined statistical distribution, and calculating the relative binding affinity of the targets from the remaining data. The resulting data can be displayed as an image with the intensity in each region varying according to the binding affinity between targets and probes.

Pattern matching can be performed manually, or can be performed using a computer program. Methods for preparation of substrate matrices (e.g., arrays), design of oligonucleotides for use with such matrices, labeling of probes, hybridization conditions, scanning of hybridized matrices, and analysis of patterns generated, including comparison analysis, are described in, for example, U.S. Pat. No. 5,800,992.

In another screening method, the test sample is assayed for the level of polypeptide of interest. Diagnosis can be accomplished using any of a number of methods to determine the absence or presence or altered amounts of a differentially expressed polypeptide in the test sample. For example, detection can utilize staining of cells or histological sections (e.g., from a biopsy sample) with labeled antibodies, performed in accordance with conventional methods. Cells can be permeabilized to stain cytoplasmic molecules. In general, antibodies that specifically bind a differentially expressed polypeptide of the invention are added to a sample, and incubated for a period of time sufficient to allow binding to the epitope, usually at least about 10 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g. fluorescein, rhodamine, Texas red, etc.) The absence or presence of antibody binding can be determined by various methods, including flow cytometry of dissociated cells, microscopy, radiography, scintillation counting, etc. Any suitable alternative methods can of qualitative or quantitative detection of levels or amounts of differentially expressed polypeptide can be used, for example ELISA, western blot, immunoprecipitation, radioimmunoassay, etc.

Screening Assays

The cells are also useful for in vitro assays and screening to detect factors that are active on cells of the myocyte lineage. Of particular interest are screening assays for agents that are active on human cells. A wide variety of assays may be used for this purpose, including immunoassays for protein binding; determination of cell growth, differentiation and functional activity; production of factors; and the like.

In screening assays for biologically active agents, viruses, etc. the subject cells, usually a culture comprising the subject cells, is contacted with the agent of interest, and the effect of the agent assessed by monitoring output parameters, such as expression of markers, cell viability, and the like. The cells may be freshly isolated, cultured, genetically altered as described above, or the like. The cells may be environmentally induced variants of clonal cultures: e.g. split into independent cultures and grown under distinct conditions, for example with or without virus; in the presence or absence of other cytokines or combinations thereof. The manner in which cells respond to an agent, particularly a pharmacologic agent, including the timing of responses, is an important reflection of the physiologic state of the cell.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

In addition to complex biological agents, such as viruses, candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1:1 to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al., (1999) *Trends Biotechnol.* 17(12):477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) *Biotechniques* 26(1):112-225; Kawamoto et al. (1999) *Genome Res* 9(12):1305-12; and Chen et al. (1998) *Genomics* 51(3):313-24, for examples.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXPERIMENTAL

Example 1

To investigate the mechanism(s) by which bone marrow (BM), hematopoietic stem cells (HSC), and circulating cells contribute to myofiber formation in injured skeletal muscle, we analyzed the myogenic potential of mononuclear cells isolated from the skeletal muscle of untransplanted mice, of mice previously transplanted with green fluorescent protein (GFP)– expressing BM or HSC, and of mice joined by parabiosis to GFP-expressing partners. GFP+ cells were found within preparations of myofiber-associated cells highly enriched for myogenic progenitor cells, and in the interstitium of injured and uninjured muscles of transplanted or parabiotic animals. Isolated muscle-engrafted cells from BM-transplanted, HSC-transplanted, or parabiotic mice generated GFP+ myofibers in vivo when injected intramuscularly into nontransgenic secondary recipients, but in contrast to endogenous myofiber-associated cells, cells engrafting muscle following transplantation or parabiosis did not express transcripts encoding myogenic transcription factors and displayed no intrinsic myogenicity in cell culture. When co-cultured with endogenous myofiber-associated cells, however, a rare population of $CD45^-$ cells, which had engrafted in muscle following parabiosis or BM transplant but not following HSC transplant, were capable of differentiation and expressed myosin heavy-chain (MHC). These data demonstrate that clonogenic, myogenic progenitors are not replenished from BM, HSC or circulating cells, although rare $CD45^-$ cells, not derived from HSC, may engraft muscle following BM transplant or parabiosis and exhibit limited, co-culture-induced, myogenic capacity.

Therefore, to clarify the origin(s) of cell populations involved in adult myogenesis, we have compared the myogenic properties of endogenous myofiber-associated cells with those of BM-derived, HSC-derived and circulating cells that engraft skeletal muscle before or after injury. Myofiber-associated or muscle interstitial cells were isolated from BM-transplanted, HSC-transplanted, or parabiotic mice by two-step enzymatic digestion of skeletal muscle, which previously has been shown to allow significant enrichment (to >95% purity) from either resting or injured muscle of cells expressing the satellite cell-associated markers CD34 and M-cadherin. By sorting these cells on the basis of donor marker and/or cell surface marker expression and analyzing their myogenic capacity both in vivo and in vitro, we have identified significant differences in the myogenic properties of muscle-resident cell populations and of cells which home to muscle from the BM and/or circulation.

Results

BM-derived muscle-resident cells display limited myogenic activity To compare the function of endogenous and BM-derived cells resident in normal adult mouse skeletal muscle, hindlimb muscles (including tibialis anterior (TA), triceps surae (TS), and quadriceps) were dissected from normal adult mice and from BM or HSC chimeric animals. Chimeric mice used in these studies were generated by transplantation into irradiated non-transgenic recipients of unfractionated BM harvested from transgenic donor mice ubiquitously expressing GFP under the control of the constitutively active β-actin promoter. Transplanted animals were screened for hematopoietic reconstitution 4-12 weeks post-transplant and exhibited near total replacement of peripheral blood leukocytes by donor-derived $GFP^+$ hematopoietic cells (>90% $GFP^+$ peripheral blood leukocytes). Muscle was digested with collagenase, and interstitial cells were separated from the myofiber fragments and their associated cells by washing. This method yields myofiber preparations in which >95% of all nuclei are located beneath the basal lamina. Myofiber-associated mononuclear cells are then released from beneath the basal lamina of isolated fiber fragments through further digestion with collagenase/dispase.

Figure 8:
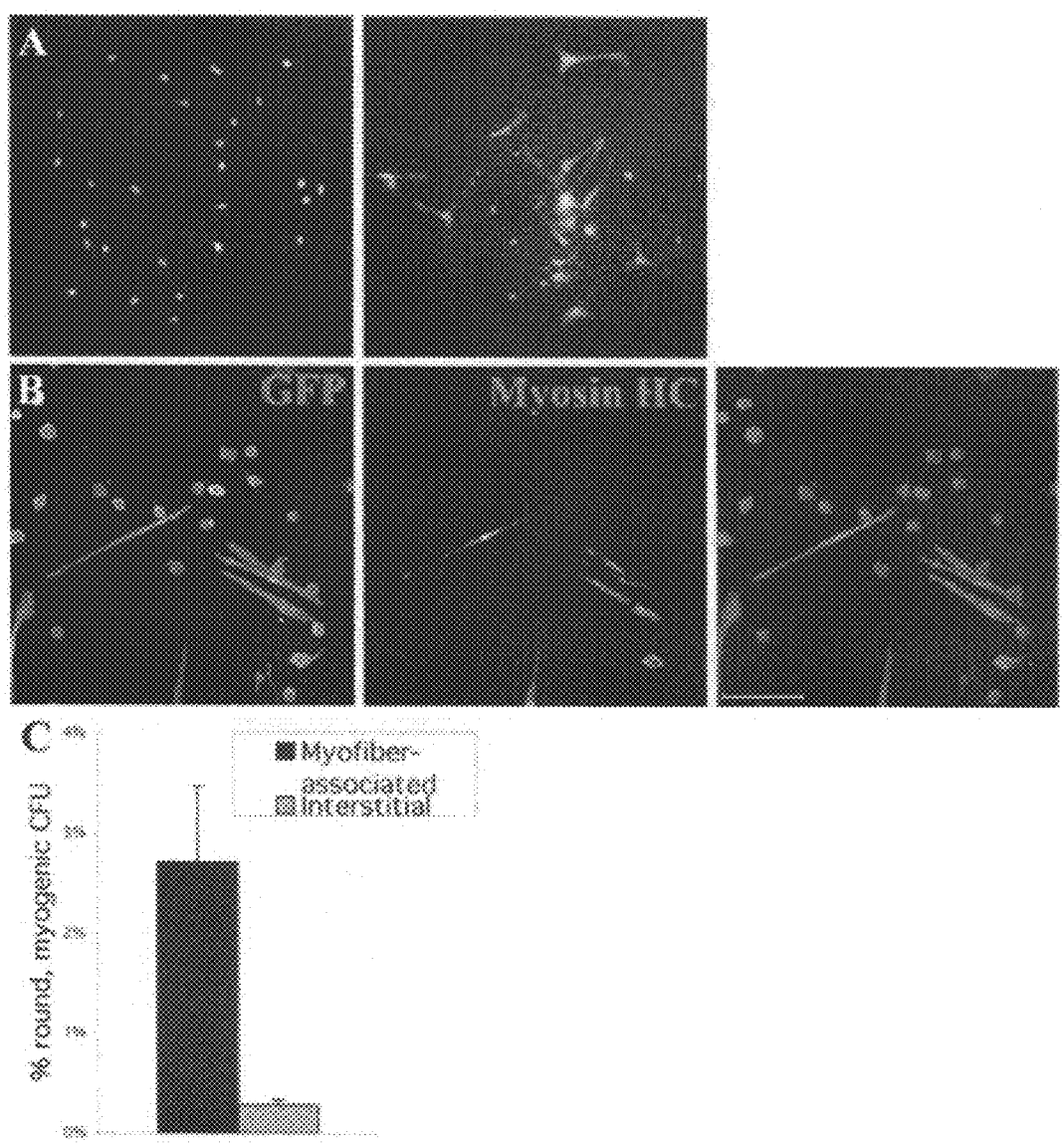
FIGS. 8A-8C. Clonogenic activity of muscle-resident mononuclear cells harvested from control (untransplanted) mice. Myofiber-associated or muscle interstitial cells were isolated by sequential enzymatic digestion and analyzed for the ability to form myogenic colonies in vitro. (A) Representative micrographs of colony morphologies observed following in vitro culture in growth medium of myofiber-associated GFP+ cells from a control (untransplanted) GFP+ transgenic animal are shown. Approximately 2.7% of plated cells formed small, round colonies (left), while 7.5% formed large fibroblast-like colonies (right). (B) Representative micrograph showing in vitro myogenic differentiation of cells forming small, round colonies. Following culture in growth medium for 7-9 days, then in fusion medium for 2 days, cells were analyzed by fluorescence microscopy for co-expression of GFP and myosin heavy-chain (MHC). Left column, GFP, middle column, MHC; right column, electronically merged image with myosin heavy-chain shown in red, GFP shown in green, and Hoechst 33342 staining of nuclei shown in blue; scalebar=100 μm (C) Relative frequency of cells capable of forming small, round, myogenic colonies among myofiber-associated and interstitial cell populations. Data are plotted as the mean percent colony forming cells (CFC)+SD.

When isolated from control, untransplanted GFP transgenic animals, myofiber-associated cells formed colonies under myogenic proliferation conditions at a frequency of ~10% of input cells. These colonies could be classified into two morphologically distinct types: ~26.5% formed colonies of small, round cells, and ~73.5% formed colonies of large, fibroblast-like cells (FIG. 8A). Upon induction of myogenic differentiation, round colonies, but not fibroblast-like colonies, contained cells which induced expression of myosin heavy-chain (MHC) and fused to form multinucleated myotubes (FIG. 8B).

Figure 9:
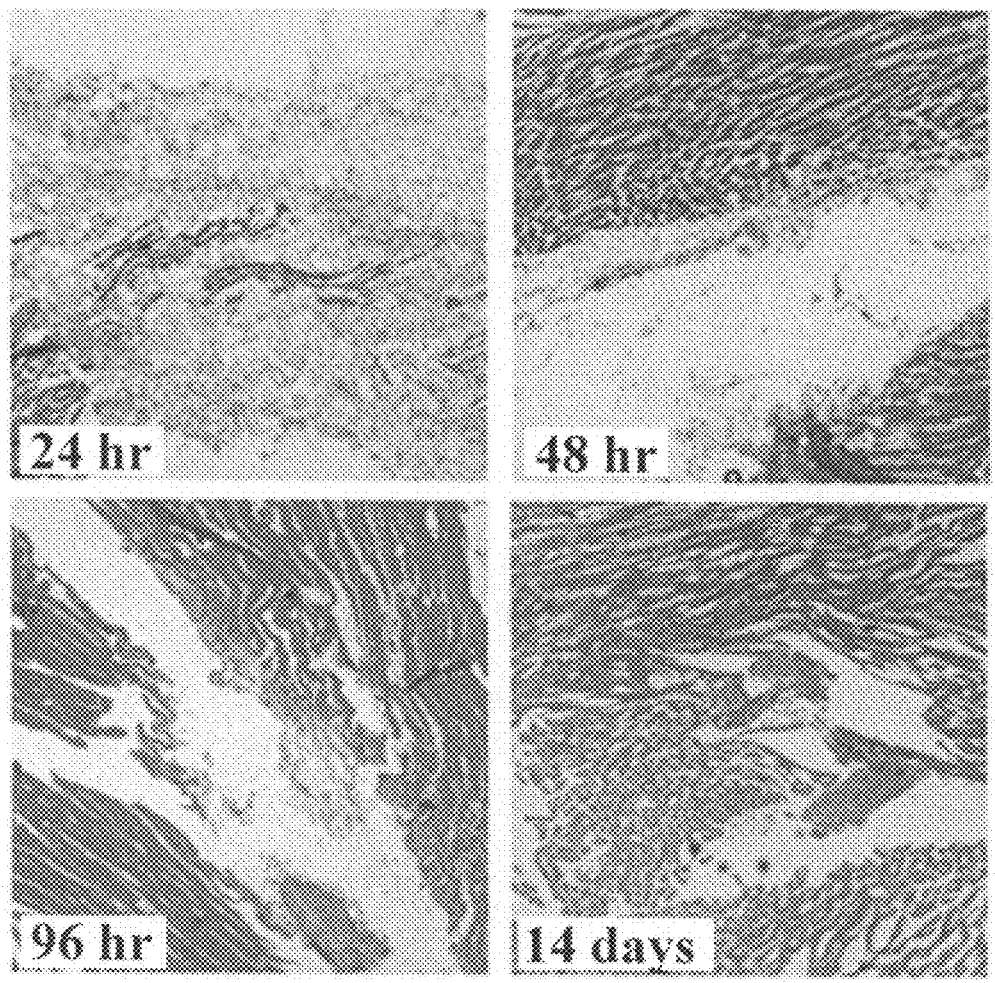
FIG. 9. Hematoxylin/eosin staining of cardiotoxin-treated muscle 24 hours, 48 hours, 96 hours, and 14 days after injury, showing regions of necrotic and regenerating muscle.

Consistent with previous reports suggesting that clonogenic, myogenic cells localize preferentially beneath the basal lamina of muscle fibers, myogenic colony-forming activity was enriched ~10-fold in the myofiber-associated, as compared with the interstitial, compartment (FIG. 8C). To determine whether BM cells generate myogenic cells in skeletal muscle following transplant, we first assessed whether BM-derived cells expressing satellite cell-associated markers could be found beneath the basal lamina of muscle fibers in transplanted animals. Because in most cases tissue damage has been required to elicit BM contributions to skeletal muscle in vivo, muscles from both uninjured mice and animals injured two days previously by intramuscular injection of cardiotoxin (2d CDTX) were examined. Although CDTX causes complete necrosis of the muscle immediately adjacent to the injection site (FIG. 9), in addition to an inflammatory response, surviving myofibers in the surrounding region display increased proliferation of satellite cells, allowing analysis of myofiber-associated and interstitial cells in this regenerating muscle.

We therefore isolated and analyzed by flow cytometry myofiber-associated and interstitial cells from injured and uninjured skeletal muscle of BM-transplanted animals. Flow cytometric analysis of both injured and uninjured muscle of BM-transplanted animals revealed donor-derived GFP+ cells in both the myofiber-associated and interstitial cell compartments (FIG. 1A), consistent with earlier suggestions that infiltrating leukocytes may invade beneath the basal lamina of damaged muscle fibers. The presence in BM-transplanted mice of GFP+ sublaminar cells, and of GFP+ cells co-expressing the satellite cell-associated markers M-cadherin and CD34, was further demonstrated by immunofluorescence and confocal microscopic analysis of frozen sections of injured and uninjured triceps surae (TS) muscles harvested from animals transplanted with GFP+ BM cells (FIG. 1B, C).

Figure 2:
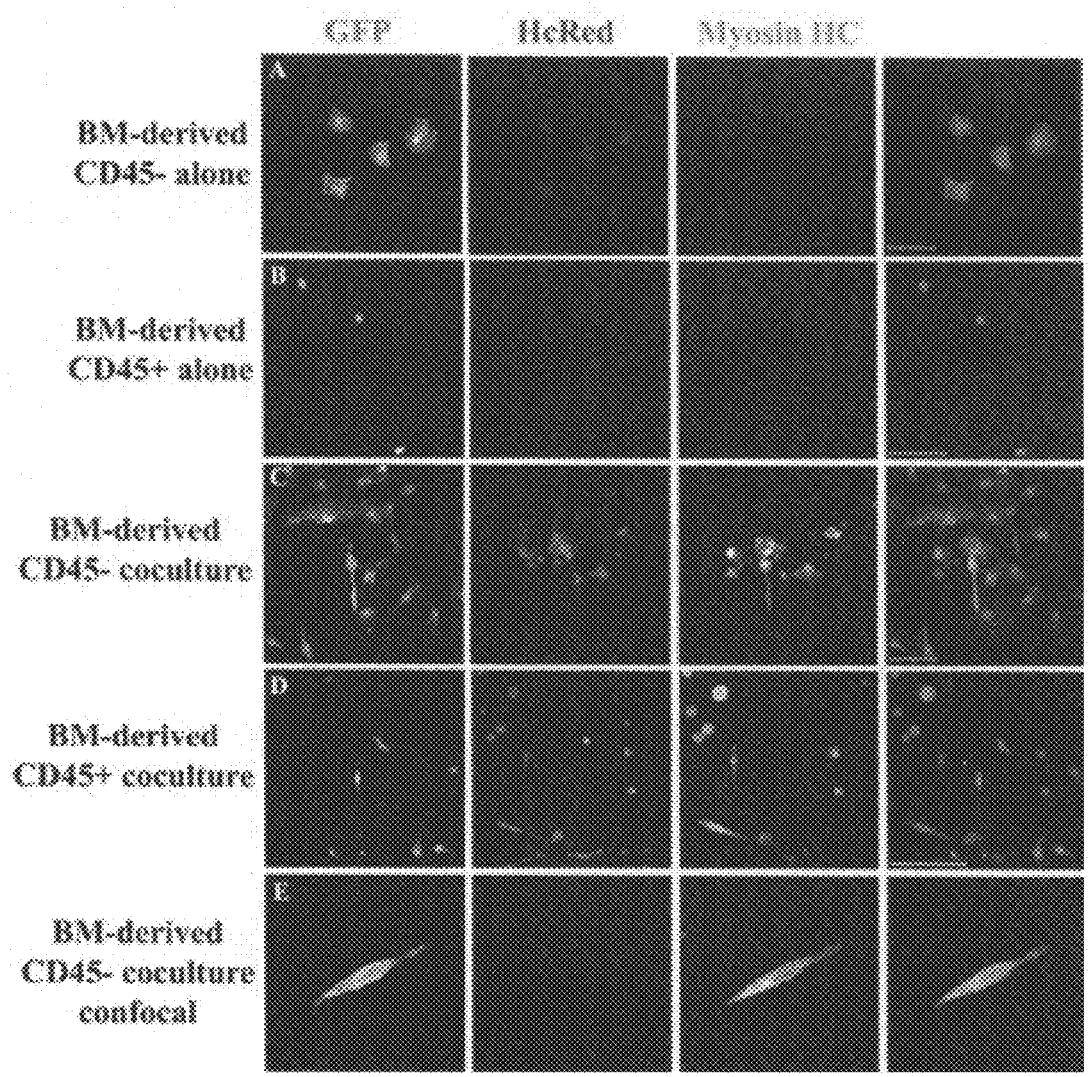
FIGS. 2A-2E. Representative micrographs of in vitro myogenic differentiation of muscle-engrafted cells. BM-derived GFP⁺ CD45⁺ or GFP⁺ CD45⁻ were isolated by FACS from myofiber-associated cell preparations of injured skeletal muscle from BM-transplanted mice. Myofiber-associated GFP⁺ CD45⁻ (A, C, E) or GFP⁺ CD45⁺(B, D) cells were isolated by FACS and cultured either alone (A, B), or together with HcRed-expressing myofiber-associated cells from an HcRed transgenic animal (B, D, E), in growth medium for 7-9 days then in fusion medium for 2 days. Cells subsequently were analyzed by standard fluorescence microscopy (A-D) or confocal microscopy (E) for co-expression of GFP, HcRed and myosin heavy-chain (MHC). First column, GFP, second column, HcRed; third column, MHC, fourth column, electronically merged image with GFP shown in green, HcRed shown in blue, and myosin heavy-chain shown in red, scalebar=100 μm.

CDTX injury increased the percentage of BM-derived GFP+ myofiber-associated and interstitial cells (FIG. 1A), ~10-fold and 3-fold, respectively, likely reflecting an injury-induced recruitment of inflammatory cells; however, despite localization of BM-derived cells in the same anatomical compartment as muscle satellite cells and expression of satellite cell-associated markers by a subset of these cells, FACS-isolated, myofiber-associated, BM-derived cells from either injured or uninjured muscle displayed no in vitro colony-forming ability and did not differentiate into MHC-expressing cells when cultured under myogenic conditions (FIG. 2A, B). In contrast, under identical conditions, GFP− (host-derived) cells did form small, round myogenic colonies that induced expression of MHC in differentiation medium. Thus, in this system, BM-derived, muscle-engrafted cells do not adopt myogenic cell fates on their own, whereas endogenous muscle precursors do so robustly.

Co-culture induced myogenic potential of BM-derived cells. In order to determine whether BM-derived, muscle-homed cells may be induced to adopt muscle fates in a myogenic environment, we also performed in vitro co-cultures of GFP+ BM-derived cells, isolated by fluorescence activated cell sorting (FACS) from 2d CDTX-injured muscle of BM-transplanted mice, with preparations of GFP− myofiber-associated cells isolated from β-actin/HcRed transgenic donors. β-actin/HcRed transgenic mice ubiquitously express a spectrally distinct fluorescent protein (HcRed) that is easily distinguished by fluorescence microscopy from GFP and allows unique marking of both types of cells included in the co-culture. This system allows any GFP+ myocytes that arise in the co-culture via cell fusion with HcRed+ myofiber-associated cells to be identified as GFP+ HcRed+ MHC+ cells.

In contrast to the lack of myogenic potential when GFP+ BM-derived cells were cultured alone (FIG. 2A, C), co-culture of GFP+ myofiber-associated or interstitial cells isolated from 2d CDTX muscle of previously BM-transplanted mice with HcRed-expressing CDTX-treated myofiber-associated cells from an untransplanted control mouse did yield GFP+ MHC+ cells (FIG. 2C). Interestingly, this co-culture induced myogenicity of myofiber-associated cells isolated from BM-transplanted animals was restricted to the CD45− subset of GFP+ BM-derived cells (FIG. 2C); CD45+BM-derived cells were never observed to generate MHC-expressing cells in these assays (FIG. 2D).

However, only 1.09+/−0.55% of input CD45− myofiber-associated cells generated MHC-expressing cells upon co-culture, while most BM-derived CD45-cells developed fibroblast-like morphology and did not induce expression of MHC. Importantly, confocal microscopy confirmed that co-culture-induced GFP+ myocytes expressing MHC did not express HcRed, indicating that they did not arise by cell fusion (FIG. 2E). In addition, consistent with the idea that GFP+ BM-derived myofiber-associated cells can differentiate directly into MHC-expressing cells, these cells also formed GFP+ MHC+ myocytes when co-cultured with HcRed+ myofiber-associated cells even when the two cell types were physically separated by a 0.22 micron transwell filter. BM-derived GFP+ myofiber-associated or interstitial cells isolated from uninjured muscle failed to form MHC-expressing cells in co-culture; however, this failure may relate to the low viability of these cells under these culture conditions. Together, these data suggest that the myogenic environment supplied by co-culture with muscle-resident myogenic cells is sufficient to promote the expression of at least some muscle-specific proteins by a fraction of BM-derived myofiber-associated cells without fusion of these cells with muscle-resident myofiber-associated cells.

Figure 3:
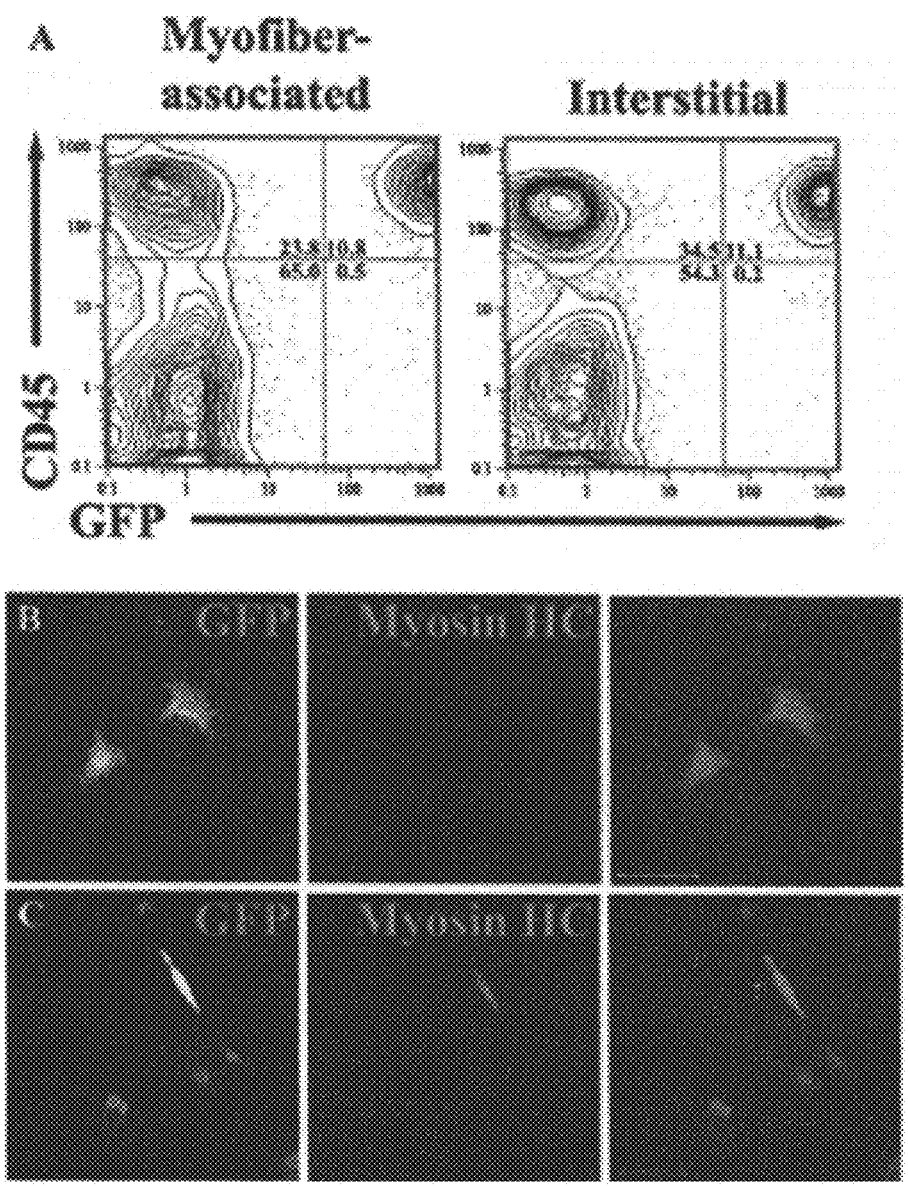
FIGS. 3A-3C. (A) Flow cytometric analysis of myofiber-associated or interstitial cells isolated from 2d CDTX-treated muscles of animals previously transplanted with 100 GFP⁺ KTLS HSC for expression of GFP and CD45. (B, C) Myofiber-associated GFP⁺ cells were isolated by FACS from 2d CDTX-treated muscles of HSC-transplanted mice and cultured either alone (B) or together with HcRed-expressing myofiber-associated cells from an HcRed transgenic animal (C), as in FIG. 2. Cells were analyzed by fluorescence microscopy for co-expression of GFP and MHC. First column, GFP, second column, MHC, third column, electronically merged image with GFP shown in green and MHC shown in red, scalebar=100 μm.

HSC and their progeny display no in vitro myogenic activity. The observation that CD45. but not CD45+BM-derived cells are capable of generating MHC-expressing cells in vitro suggests that this activity derives from a cell of non-hemato-poietic origin. However, to determine directly whether the co-culture-induced myogenic differentiation of BM cells in fact indicated lineage plasticity of HSC progeny, we also performed in vitro myogenic assays with cells isolated from muscles of non-transgenic recipients previously irradiated and transplanted with FACS-isolated c-kit+ Thy1.1$^{lo}$ Lin− Sca-1+ (KTLS) HSC. Similar to BM-transplanted animals, the muscle of CDTX-injured HSC-transplanted animals contained HSC-derived GFP+ cells in both the myofiber-associated and interstitial compartments (FIG. 3A). However, no HSC-derived muscle-resident cells expressed MHC when cultured alone (FIG. 3B) or in co-culture (FIG. 3C), indicating that the co-culture-induced myogenic activity of transplanted BM cells derives from a cell population distinct from HSC or their progeny.

Figure 4A:
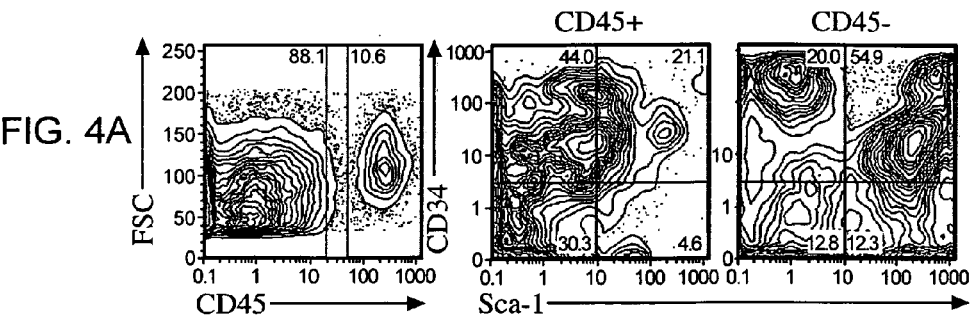
Figure 4B:
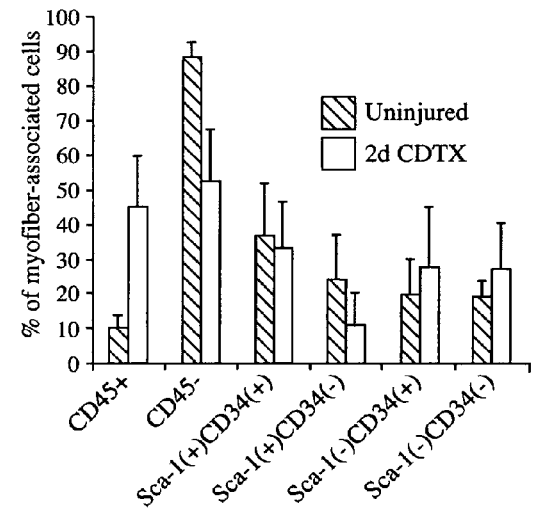

Characterization of muscle-resident cell populations with in vitro myogenic activity. To begin to characterize the BM-derived population(s) capable of co-culture-induced myogenesis, we first separated endogenous myofiber-associated cells (from untransplanted GFP transgenic mice) into distinct populations by cell surface marker expression to identify cells that exhibited clonogenic, myogenic capacity. Flow cytometric analysis of freshly isolated myofiber-associated and interstitial cell preparations from either uninjured or 2d CDTX muscles revealed that the majority of myofiber-associated cells expressed the satellite cell-associated marker CD34, while only ~50% of the cells expressed Sca-1 (FIG. 4A, B). In uninjured muscle, a small subset of myofiber-associated cells (9.1+/−3.8%) expressed the pan-hematopoietic marker CD45. The frequency of CD45$^+$ cells in the muscle increased ~4-5-fold after CDTX injury, likely due to an injury-induced influx of inflammatory cells (FIG. 4B). In both injured and uninjured muscles, most (~80-90%) CD45$^+$ myofiber-associated cells co-expressed the myeloid lineage marker Mac-1; however, other hematopoietic cell types, including itinerant hematopoietic stem cells, may also be present, and both CD45$^+$ and CD45$^-$ cells displayed heterogeneous expression of Sca-1 and CD34 (FIG. 4A).

Figure 4C:
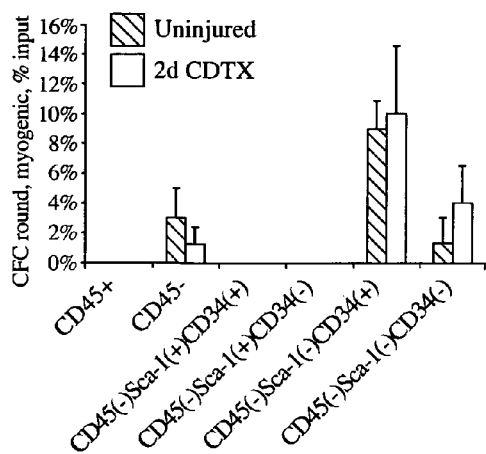
Figure 4D:
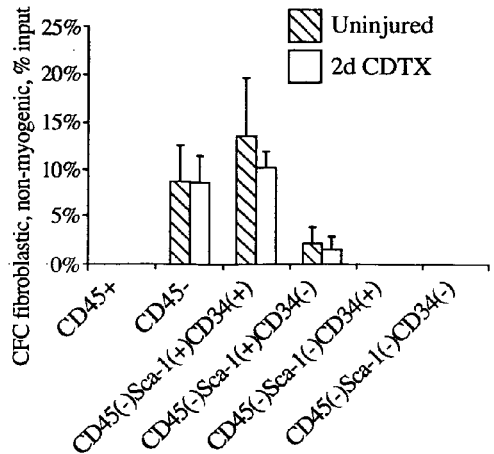
Figure 10:
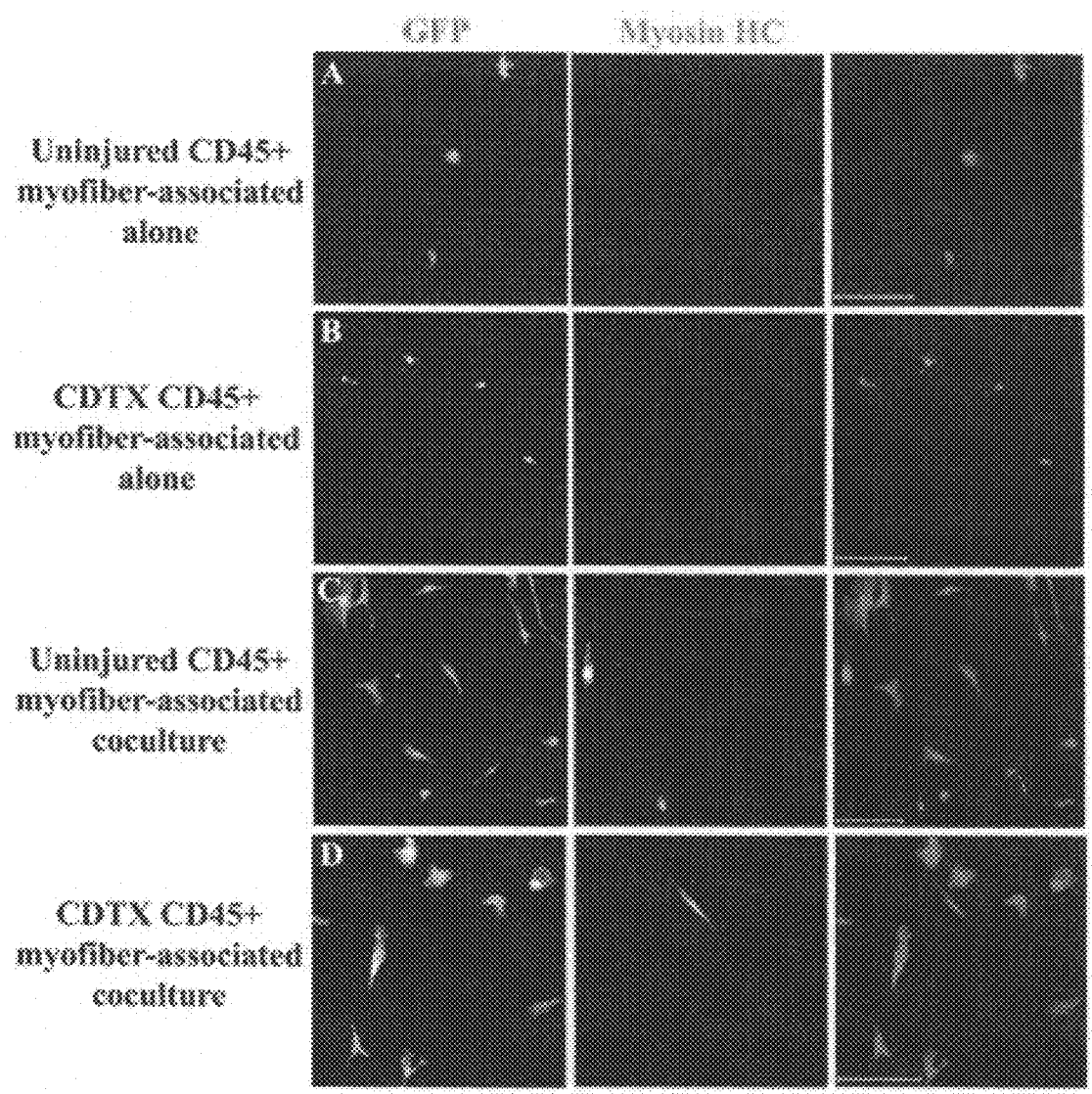
FIGS. 10A-10D. Representative micrographs of in vitro myogenic differentiation of cells isolated from the skeletal muscle of control untransplanted mice. GFP+ myofiber-associated cells were isolated by FACS from uninjured (A, C) or CDTX-injured (B, D) muscle. Sorted GFP+ CD45+ cells were analyzed for ability to form myogenic colonies in vitro following culture alone (A-B) or following co-culture with GFP− endogenous myofiber-associated cells (C-D). Cells were analyzed by fluorescence microscopy for co-expression of GFP and myosin heavy chain. Left column, GFP, middle column, MHC; right column, electronically merged image with MHC shown in red and GFP shown in green; scalebar=100 μm.

To assay the myogenic activity of each of these muscle-resident populations, we assessed the ability of FACS-purified myofiber-associated cells to form (i) colonies of round, myogenic cells, (ii) colonies of fibroblast-like, non-myogenic cells, (iii) MHC-expressing myoblasts when cultured alone, and (iv) MHC-expressing myoblasts in a co-culture system. Within the myofiber-associated compartment of either uninjured or 2d CDTX muscle of untransplanted mice, round, myogenic colony-forming ability resided exclusively in the CD45-Sca-1-cell population and was highly enriched among CD45-Sca-1-CD34$^+$ cells (FIG. 4C). In contrast, non-myogenic fibroblast-like colony-forming ability resided exclusively in the CD45-Sca-1$^+$ population and was highly enriched among CD45-Sca-1$^+$ CD34$^+$ cells (FIG. 4D). Furthermore, the ability to form MHC-expressing myocytes when cultured alone resided exclusively in the CD45-Sca-1-cell population (FIG. 4E, F), whereas CD45-Sca-1$^+$ CD34$^-$, though not CD45-Sca-1$^+$ CD34$^+$ cells, exhibited this capacity only in co-culture (FIG. 4G, H). In contrast to previous reports in this system, myofiber-associated CD45$^+$ cells from either uninjured or 2d CDTX muscle of untransplanted animals displayed no myogenic potential either alone or in co-culture assays (FIG. 10).

Figure 11:
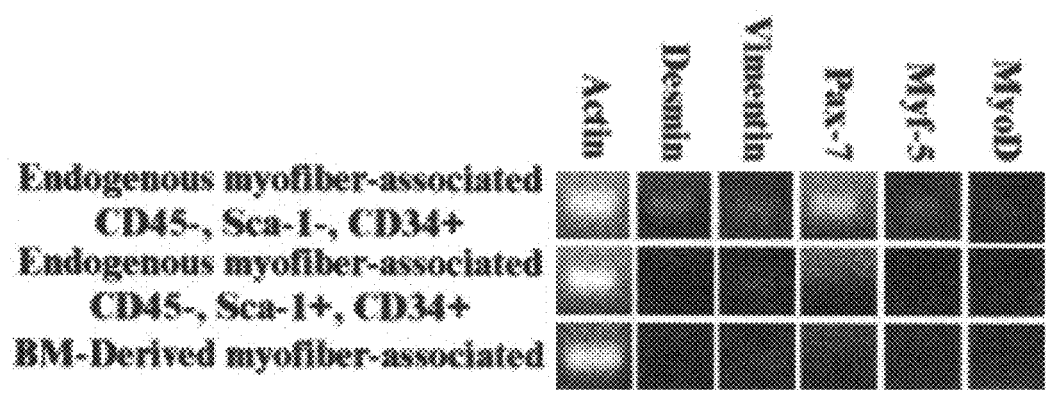
FIG. 11. RT-PCR analysis of expression of myogenic transcripts by endogenous or BM-derived cells. CD45− Sca-1− CD34+ or CD45− Sca-1+ CD34+ cells were isolated by FACS and expression of desmin, vimentin, Pax-7, Myf-5, or MyoD determined by RT-PCR from ~1667 cell equivalents. PCR products were analyzed by agarose gel electrophoresis and visualized by staining with ethidium bromide. Control reactions in which reverse transcriptase was omitted showed no product.

Finally, as in untransplanted animals, the co-culture-induced ability of BM-derived myofiber-associated cells isolated from BM-transplanted, 2d CDTX animals to form MHC-expressing myocytes was found exclusively within the CD45-Sca-1$^+$ CD34-subset of GFP$^+$ cells (FIG. 4I); however, unlike endogenous CD45-Sca-1-cells, BM-derived GFP$^+$ CD45-Sca-1-cells isolated from BM-transplanted mice displayed no in vitro myogenic potential. Consistent with these findings, freshly-isolated myofiber-associated CD45-Sca-1-CD34$^+$ cells expressed mRNA encoding the myogenic intermediate filament protein desmin, the myogenic transcription factors MyoD, Myf-5, and Pax-7, and the fibroblast-expressed focal adhesion protein vimentin, while CD45-Sca-1$^+$ CD34$^+$ cells expressed only vimentin (FIG. 11). Similarly, and consistent with their generation of predominantly fibroblast-like colonies in culture, BM-derived GFP$^+$ myofiber-associated cells expressed vimentin, but not desmin, MyoD, Myf-5, or Pax-7 (FIG. 11). Thus, in normal skeletal muscle, formation of clonogenic, myogenic colonies in vitro and expression of myogenic transcripts are largely restricted to the CD45$^-$ Sca-1$^-$ CD34$^+$ subset of cells, which are not BM-derived and comprise only ~20-30% of myofiber-associated cells in uninjured muscle (FIG. 4).

In vivo contributions of BM-derived or endogenous muscle-resident cells to skeletal muscle. To assess further the myogenic activity of myofiber-associated and interstitial cells isolated from untransplanted or BM-transplanted animals, we assayed directly their contribution to myofiber formation in vivo, following intramuscular injection. GFP$^+$ cells were isolated by FACS from myofiber-associated or interstitial cell preparations of uninjured or 2d CDTX-injured muscle of untransplanted, GFP transgenic mice or of mice transplanted previously with GFP$^+$ BM cells or HSC. The sorted cells then were injected into the TS muscle of control, non-transgenic animals that had been injured one day previously by intramuscular injection of cardiotoxin (1d CDTX).

Figure 5:
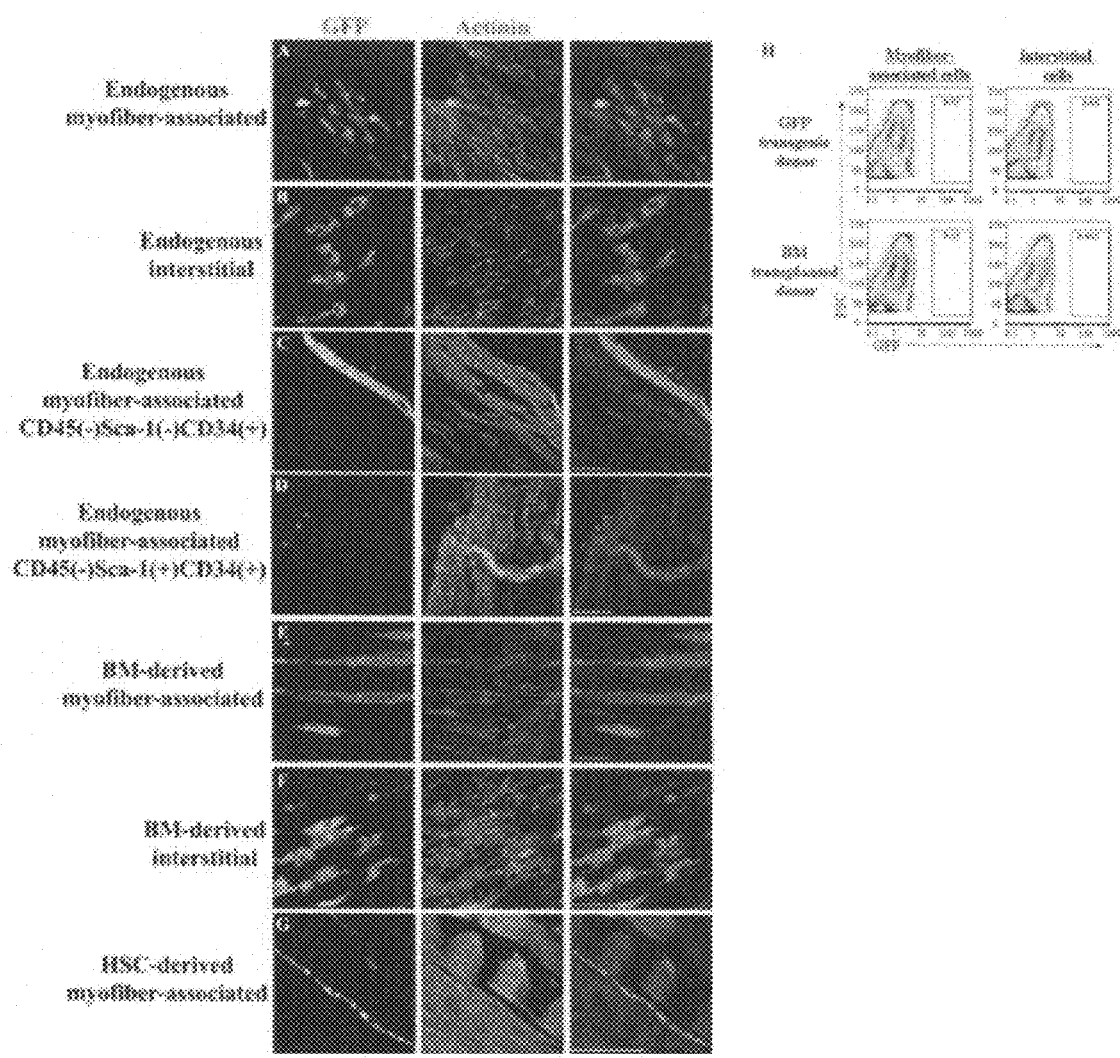
FIGS. 5A-5H. Representative micrographs of in vivo myofiber cluster formation (A-G) and FACS analysis of myofiber-associated cells (H) after intramuscular injection of the indicated cell populations. Myofiber-associated (A, C-E, G) or muscle interstitial (B, F) cells were isolated from 2d CDTX-injured skeletal muscle of control (untransplanted) GFP⁺ transgenic mice (A-D) or from muscle of a recipient of a GFP⁺ BM cell transplant (E, F) or HSC transplant (G). Sorted GFP+ cells (A, B, E-G), GFP+ CD45− Sca-1− CD34+ (C) or GFP+ CD45− Sca-1+ CD34+ (D) cells were injected intramuscularly into 1d CDTX-injured muscles of non-transgenic recipient animals and two weeks later, muscles were analyzed by immunofluorescence for the presence of GFP-expressing myofibers. Left column, GFP; middle column, α-actinin; right column, electronically merged image with GFP shown in green, α-actinin shown in red, and Hoechst 33342 staining of nuclei shown in blue; scalebar=100 μm. (H) Flow cytometric analysis of myofiber-associated cells isolated from 1d CDTX-injured muscle two weeks after intramuscular injection of GFP+ myofiber-associated (left column) or interstitial (right column) cells from a control (untransplanted) GFP+ transgenic animal (top row) or an animal previously transplanted with GFP+ BM cells (bottom row). Data are shown as contour plots of live cells isolated from the myofiber-associated compartment of intramuscularly injected animals two weeks after injection. The percent of cells that fall within the indicated gate (GFP+ cells) is as indicated.

After two weeks, injured muscles were harvested and analyzed by cryosectioning and immunofluorescence microscopy to identify GFP$^+$ myofibers in the regenerating muscle. Both myofiber-associated cells and interstitial cells isolated from GFP transgenic animals robustly contributed to clusters of GFP$^+$ myofibers upon intramuscular transfer to 1d CDTX-injured recipients (FIG. 5A, B). Consistent with in vitro assays, CD45$^-$ Sca-1$^-$ CD34$^+$, but not CD45$^-$ Sca-1$^+$ CD34$^+$, myofiber-associated cells contributed to myofibers in vivo upon intramuscular injection (FIG. 5C, D). Both myofiber-associated and interstital cells from BM-transplanted animals also contributed to myofibers in vivo (FIG. 5E, F). Furthermore, HSC-derived muscle-resident cells also were able to contribute to myofibers in vivo (FIG. 5G), despite the fact that these cells were uniformly non-myogenic when assayed in vitro (FIG. 3B, C). However, the ability to generate donor-marker expressing myofibers following intramuscular injection appeared to be a unique property of BM-derived cells that had migrated to and engrafted in the myofiber-associated or muscle interstitial cell compartments, as intramuscular injection of splenic Mac-1$^+$ and/or Gr-1$^+$ cells, freshly isolated unfractionated BM. 14 cells, or FACS-purified KTLS HSC failed to yield any donor-marker expressing myofibers in this assay (Table 1).

TABLE 1

Muscle chimerism in intramuscularly injected cardiotoxin injured animals.

| Donor cells | # cells injected | #GFP + myofibers in CDTX TS | # total myofibers examined | % GFP + myofibers |
|---|---|---|---|---|
| BM | 10$^6$ | 0 | 18,906 | 0 |
|  |  | 0 | 33,440 | 0 |
|  |  | 0 | 23,665 | 0 |
|  |  | 0 | 93,762 | 0 |
|  | 2 × 10$^7$ | 0 | 51,841 | 0 |
|  |  | 0 | 90,305 | 0 |
|  |  | 0 | 69,915 | 0 |
|  |  | 0 | 86,832 | 0 |
|  |  | 0 | 59,431 | 0 |
| Data summary | | Frequency of mice with chimeric muscles: 0/9 Overall % of GFP + myofibers: 0/528,097 (0%) | | |
| HSC | 3000 | 0 | 55,718 | 0 |
|  |  | 0 | 45,916 | 0 |
|  |  | 0 | 27,684 | 0 |
|  |  | 0 | 25,916 | 0 |
| Data summary | | Frequency of mice with chimeric muscles: 0/4 Overall % of GFP + myofibers: 0/155,234 (0%) | | |
| Splenic Mac-1$^+$Gr-1$^+$ | 10$^6$ | 0 | 12,200 | 0 |
|  |  | 0 | 3,200 | 0 |
| Data summary | | Frequency of mice with chimeric muscles: 0/2 Overall % of GFP + myofibers: 0/15,400 (0%) | | |

To obviate potential inefficiency in the homing of BM myogenic cells to muscle, the TS muscles of non-transgenic, non-transplanted mice were injured by cardiotoxin (CDTX)

injection and 1 day later, GFP⁺ unfractionated BM cells, FACS purified GFP⁺ unfractionated BM cells, FACS purified GFP⁺ KTLS HSC, or splenic Mac-1+Gr-1⁺ cells were injected intramuscularly into the site of injury. This strategy has previously been reported to yield substantial incorporatin of donor marker expressing myofibers following transfer into cardiotoxin-injured muscle of immunodeficient mice (Ferrari et al., 1998). Eight weeks following injury, muscles were examined for GFP⁺ donor cell incorporation. The number and percent of detected GFP⁺ myofibers in injured and uninjured tissue are given for each animal (each line represents an individual mouse). Data are summarized as the frequency of muscle engraftment (# engrafted mice/#mice examined) and overall frequency (%) of GFP⁺ myofibers (#GFP⁺ fibers/total fibers examined).

Despite the ability of both myofiber-associated and interstitial cells from control GFP transgenic, or from BM-transplanted animals to contribute to myofiber formation in vivo, differences were apparent in the ability of cells from these two origins to home to and repopulate the myofiber-associated compartment following intramuscular injection. When myofiber-associated cells were isolated from the muscle of secondary recipients two weeks after intramuscular injection of either myofiber-associated or interstitial cells and analyzed by flow cytometry, cells originally isolated from the myofiber-associated compartment, but not from the interstitial cell compartment, of either GFP transgenic or BM-transplanted mice re-localized to the myofiber-associated compartment (FIG. 5H). Yet, following culture of these re-isolated cells from intramuscularly injected secondary recipients, only myofiber-associated cells from GFP transgenic animals were competent to autonomously form in vitro colonies of cells that differentiated into MHC⁺ myocytes. Intramuscular injection of cells directly isolated from BM did not yield engraftment into the myofiber-associated cell compartment, suggesting that some component of the process of BM transplantation (e.g., irradiation, intravenous injection, long-term reconstitution of hematopoiesis, etc.) may be necessary for localization of these cells to this compartment. Thus, both endogenous and BM-derived myofiber-associated cells possess the ability to re-home to the myofiber-associated compartment, yet only endogenous cells, and not those derived from transplanted BM, exhibit myogenic colony-forming potential upon re-isolation.

Cells with intrinsic myogenic activity do not transit through the bloodstream, but cells with co-culture-induced myogenic potential do. Finally, to address the issue of whether any circulating cells act as myogenic progenitors in skeletal muscle, we analyzed the in vitro and in vivo myogenic capacity of GFP⁺ cells cross-engrafting into muscle in parabiotic mice generated by surgical joining of GFP transgenic and non-transgenic mice. Parabiosis results in the development of a common, anastomosed vasculature joining the two animals, with cross-circulation detectable within 2-3 days of joining. Because parabiotic mice are joined only through their shared circulation, these parabiosis experiments assay the existence of any circulating cells with myogenic potential capable of engraftment in muscle. As in BM-transplanted mice, GFP⁺ cells could be identified in the myofiber-associated and interstitial compartments of 2d CDTX-treated skeletal muscle of non-transgenic parabiotic partners in GFP⁺::GFP⁻ pairs (FIG. 6A), but these cells were uniformly non-myogenic when cultured alone (FIG. 6B).

Figure 6:
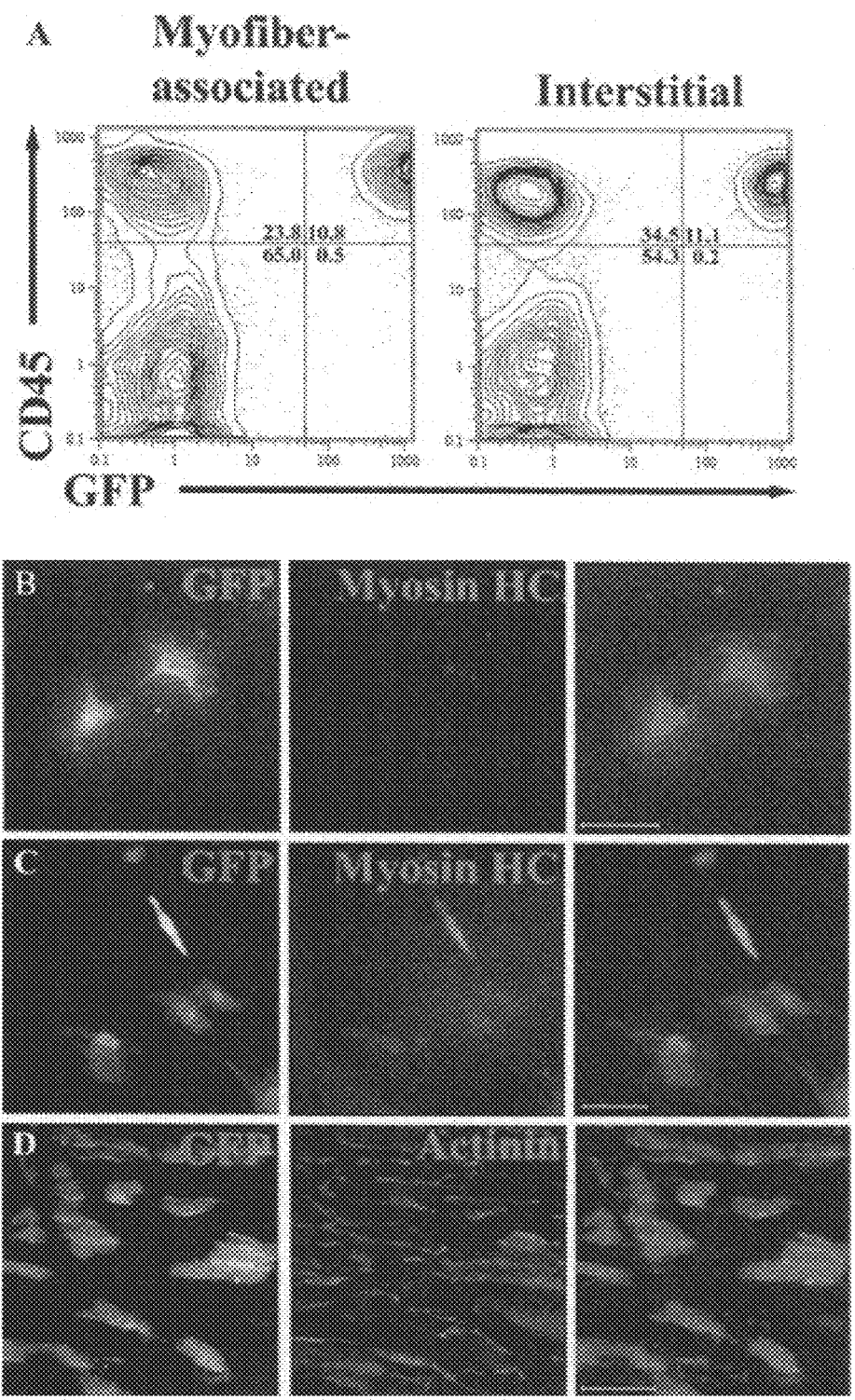
FIG. 6A-6D. (A) Flow cytometric analysis of GFP and CD45 expression by myofiber-associated and interstitial cells isolated from 2d CDTX-treated muscles of non-transgenic animals parabiosed to GFP-expressing partners. (B-D) Representative micrographs of in vitro myogenic differentiation of cells isolated from the skeletal muscle parabiotic mice. GFP+ myofiber-associated cells were isolated by FACS from the CDTX-injured muscle the non-transgenic parabiotic partner of a GFP+ transgenic animal. Sorted GFP+ cells were analyzed for ability to form myogenic colonies in vitro following culture alone (B) or following co-culture with GFP− endogenous myofiber-associated cells from the same muscle (C), cells were analyzed by fluorescence microscopy for co-expression of GFP (left column) and myosin heavy-chain (MHC, middle column). (D) Sorted GFP+ cells were assayed for the ability to contribute to GFP+ myofibers in vivo following intramuscular injection into 1d CDTX recipients, as in FIG. 5. Left column, GFP; middle column, MHC, right column, electronically merged image with myosin heavy-chain shown in red, GFP shown in green, and Hoechst 33342 staining of nuclei shown in blue; scalebar=100 μm.

Cross-engrafting GFP⁺ cells did possess co-culture-induced myogenic activity (FIG. 6C) and contributed to myofibers in vivo after intramuscular injection (FIG. 6D). Thus, in all aspects tested, cells engrafting from circulation behaved identically to BM-derived muscle-homing cells, suggesting that irradiation and transplantation are not required for the engraftment of these cells into muscle. In addition, these data strongly suggest that progenitors with the full myogenic potential of endogenous muscle-resident cells do not normally transit through the bloodstream and are not seeded from circulating precursors in the adult animal.

Discussion

Figure 7:
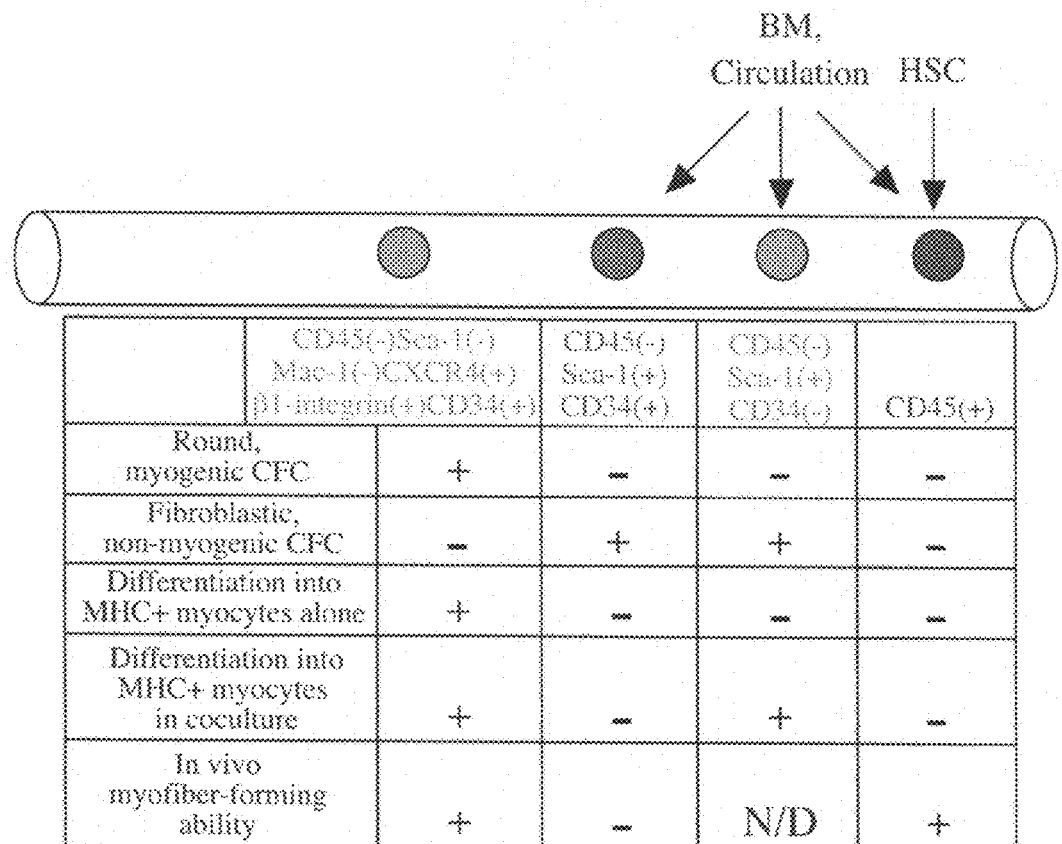
FIG. 7. Origins and hierarchy of myogenicity among cells present in adult skeletal muscle.

Recently, the notion has been called into question that a uniform population of somite-derived, sublaminar satellite cells is the only adult muscle regenerative unit. To assess the myogenic potential of muscle-resident cells before and after injury, we have utilized a procedure that separates muscle-resident cells into a myofiber-associated compartment highly enriched for satellite cells, and a separate interstitial cell preparation, allowing direct analysis of these different cells' myogenic potential. As criteria for myogenicity, we have evaluated (i) expression of myogenic proteins; (ii) autonomous in vitro myogenic colony-forming capacity; (iii) myogenic capacity in co-culture with isolated muscle-resident myogenic cells; (iv) in vivo contribution to myofibers in injured muscle; and (v) engraftment of the myofiber-associated compartment in vivo following intramuscular injection and subsequent maintenance of myogenic-colony forming capacity. Our studies reveal that the only cells in muscle that fulfill all of the above criteria of classically defined satellite cells are endogenous (not derived from BM, HSC or circulating cells), CD45-Sca-1-CD34⁺ myofiber-associated cells. Around 20-30% of myofiber-associated cells have this phenotype, yet only ~10% of these cells display clonogenic, myogenic ability (FIG. 4), suggesting that these cells are unlikely to represent a completely homogeneous population. Intriguingly, the myofiber-associated cell compartment contains not only these fully myogenic cells but also several distinct cell populations with limited or no myogenic capacity. These include: (i) CD45-CD34⁺ Sca-1⁺ cells, which express vimentin and form fibroblast-like colonies, (ii) CD45⁻ CD34⁺ Sca-1⁻ cells, some of which generate MHC-expressing cells when co-cultured with endogenous myogenic cells and which are responsible for BM-derived coculture-induced myogenesis, and (iii) CD45⁺ cells, most of which are Mac-1+myeloid lineage cells derived from BM HSC that possess no myogenic activity in vitro (FIG. 7).

The ability to sort these distinct populations freshly from muscle facilitates determination of cell lineage relationships in the differentiation of muscle stem cells and progenitors as well as the determination of the signaling pathways and gene expression dynamics important for maintaining muscle-resident cell populations. While BM-derived myofiber-associated cells cannot form myogenic colonies on their own, at least some BM-derived, CD45⁻ cells do generate donor-marker expressing MHC⁺ myoblasts and myotubes when co-cultured with myogenic cells. This co-culture-induced myogenic activity does not derive from HSC or their progeny, as HSC-derived muscle-resident cells do not display myogenic activity either alone or in co-culture experiments. The induction of expression of muscle-specific markers by BM-derived cells in vitro occurs in the absence of cell fusion, suggesting that limited myogenic differentiation or conversion of BM cells may occur through the process of transplantation, muscle homing, engraftment in the myofiber-associated fraction and/or subsequent isolation and culture.

This finding does not exclude the possibility that cell fusion is required for the in vivo contribution of BM-derived cells to myofibers in injured muscle of transplanted animals. BM-derived cells isolated from the myofiber-associated compartment of injured muscle are also able to form clusters of myofibers and re-enter the myofiber-associated compartment upon intramuscular injection into secondary recipients. Thus, donor marker-expressing BM-derived cells that engraft in the muscle following intravenous transfer into irradiated recipient mice, at least some of which can be confirmed by immunostaining to localize beneath the basal lamina, compose a functionally distinct population of cells occupying the classically defined satellite cell compartment. Their lack of intrinsic myogenic colony-forming ability suggests a relative lack of myogenic specification as compared to endogenous myofiber-associated cells.

These data indicate that a significant fraction of myofiber-associated cells, particularly in injured muscle, do not display robust myogenic potential in vitro. Even in the absence of injury, a large population of $CD45^+Mac-1^+$ cells resides in the muscle; these cells are not quickly replenished from the bloodstream, as they remain predominantly host-derived in muscles of parabiotic mice, which exhibit ~50% chimerism of circulating blood leukocytes (FIG. 6A). Thus, their role may be equivalent to Langerhans cells in the skin and microglia in the brain, which act as local tissue-resident immune cells.

In contrast, $CD45^- Sca-1^+ CD34^+$ cells, which are clonogenic, but uniformly non-myogenic, may act as progenitors for mesenchymal lineages that reside in close proximity to muscle, such as fibroblasts, fat, tendon, and cartilage. Although this remains to be demonstrated directly, preliminary experiments indicate that these cells undergo adipogenesis at a higher frequency than myogenic colony-forming cells. The low percentage of BM-derived and HSC-derived myofibers detected in previous studies, combined with the rarity and reduced myogenic capacity of BM-derived muscle-resident cells in vitro, strongly suggests that endogenous cells carry out the majority of muscle regeneration in response to injury. In spite of their lesser role in contribution to muscle repair, the myogenic capacity and homing ability revealed within BM-derived populations found in the muscle following transplantation are not general properties of BM-resident cells or splenic macrophage populations.

Additionally, the co-culture-induced myogenic activity of BM- but not HSC-derived myofiber-associated cells indicates a role for non-HSC-derived BM cells capable of engrafting muscle. As bone marrow-derived mesenchymal stem cells but not HSC share this co-culture-induced myogenic ability, BM-derived muscle-engrafted cells may be the progeny of mesenchymal stem cells.

Experimental Procedures

Mice and Antibodies. C57BL/Ka mice were bred and maintained at the Stanford University Research Animal Facility. Enhanced green fluorescent protein (GFP) transgenic mice were generated as described (Wright et al. (2001) Science 294, 1933-6), and were backcrossed for at least ten generations to C57BL/Ka-Thy-1.1 mice. GFP transgenic mice used as BM donors in these studies were 6-12 weeks old, and non-transgenic recipients of transplanted cells were 10-14 weeks old. For parabiosis, animals were typically joined at 6-8 weeks of age. HcRed transgenic mice were generated using a modified pCXEGFP vector (pCXHcRed) in which the eGFP cDNA was replaced by cDNA encoding HcRed (Clonetech, Palo Alto, Calif.). The construction of the pCXEGFP vector and its use in generating eGFP transgenic mice have been described previously. To generate HcRed transgenic mice, pCXHcRed was linearized, and the fragment containing the cytomegalovirus-immediate early (CMV-IE) enhancer, chicken .beta.-actin promoter, eGFP complementary DNA (cDNA), and .beta.-globin polyadenylation sequences was gel purified using the Qiaquick gel extraction kit (QIAGEN™, Valencia, Calif.). Purified, linearized DNA was injected into F1 zygotes from crosses C57BL/Ka-Thy1.1.times.C3H mice, and founder mice were screened by PCR and flow cytometry.

Transplanted recipient β-actin/HcRed mice used in these studies were backcrossed for 2 generations to C57BL/Ka-Thy-1.1 mice. The antibodies used in these studies included anti-Sca-1 (Ly6A/E, PE or Texas Red conjugate), polyclonal anti-GFP (Alexa488 conjugate, Molecular Probes, Eugene, Oreg.), MY-32 (anti-skeletal myosin (fast), Sigma, St. Louis, Mo.), NOQ7.5.4D (anti-skeletal myosin (slow), Sigma), 30-F11 (anti-CD45, APC conjugate, BD Pharmingen, San Diego, Calif.), anti-laminin, anti-M-cadherin (BD.21 Pharmingen), biotin anti-mouse IgG (VectorLabs), streptavidin Alexa-594 conjugate (Molecular Probes), anti-CD34 biotin-conjugate (BD Pharmingen), anti-B220, anti-CD3, anti-Mac-1, anti-Gr-1. Unless otherwise indicated, mAb were produced and purified in this laboratory.

BM harvesting. To harvest BM cells, femur, fibula and/or tibia of donor mice were crushed using a mortar and pestle in HANKS' Balanced Salt Solution (Invitrogen) supplemented with 2% FCS and 2 mM EDTA. Alternatively, BM was flushed from the femurs and tibiae of donor mice with HANKS' Balanced Salt Solution (Life Technologies) supplemented with 2% FCS and 2 mM EDTA. Red blood cells subsequently were lysed during a 3 minute incubation in 0.15 M ammonium chloride, 0.01M potassium bicarbonate solution on ice. BM cell suspensions were filtered through nylon mesh prior to transplantation.

Fluorescence activated cell sorting (FACS) of HSC. $GFP^+$ HSC were isolated by double FACS sorting of c-kit-enriched bone marrow from GFP transgenic mice, based on previously defined reactivity for particular cell surface markers ($c-kit^+$ $Thy1.1^{lo}$ $Lin^-$ $Sca-1^+$, KTLS) (Morrison et al. (1997) Development 124, 1929-39). All antibody incubations were performed on ice for 15-25 minutes. BM cells were first stained with purified lineage antibodies followed by anti-rat Cy5PE (Caltag, Burlingame, Calif.). Lineage stained cells were further stained for c-kit with biotinylated 3C11 and c-kit positive cells were enriched by positive selection using MACS (Miltenyi Biotec, Sunnyvale, Calif.) streptavidin-conjugated magnetic beads and AutoMACS cell separator columns according to manufacturer's instructions. c-kit enriched cells were stained with fluorescently labeled 2B8, 19XE5, and E13-161.7 monoclonal antibodies to identify HSC. 3C11 and 2B8 recognize distinct, non-overlapping epitopes of c-kit. Prior to FACS analysis cells were suspended in 1 µg/ml of propidium iodide (PI) to identify and exclude dead ($PI^+$) cells. KTLS HSC populations were double sorted to ensure purity, using a highly modified Vantage SE (Becton Dickinson Immunocytometry Systems, Mountain View, Calif.), provided by the Stanford University Shared FACS Facility. Flow cytometry data was analyzed using FlowJo (Treestar, San Carlos, Calif.) analysis software.

BM transplantation. Recipient mice received a lethal dose of irradiation (950Rad, delivered in a split dose three hours apart) prior to transplantation with $GFP^+$ cells by retroorbital injection. Recipient mice were transplanted with $1 \times 10^7$ or $5 \times 10^7$ $GFP^+$ BM cells, or with 100 sorted $GFP^+$ KTLS HSC. B cells, T cells and myeloid cells in the PB were identified by flow cytometry using anti-B220, anti-CD3, or anti-Mac-1/anti-Gr-1, respectively. All transplanted mice showed high level chimerism (>90% $GFP^+$ cells) of peripheral blood leukocytes. BM-transplanted mice were subjected to muscle injury and regeneration 4-12 weeks following reconstitution.

Muscle Dissociation and FACS sorting. Myofiber-associated and muscle interstitial cells were prepared as described (Conboy et al. (2003) Science 302, 1575-7; Conboy et al. (2002) Dev Cell 3, 397-409). Animals were anaesthetized with avertin, and limb muscles, including triceps surae, tibialis anterior, quadriceps, and triceps, were dissected and placed in Dulbecco's Modified Eagle's Medium (Invitrogen, Carlsbad, Calif.)+0.2% collagenase type II (Invitrogen) at 37° C. and shaken for 1.5-2 hours. Collagenase digested muscle cells were poured onto a petri dish, and the collagenase solution was aspirated and replaced with Ham's F10 Medium (Invitrogen)+20% FBS (Irvine Scientific, Santa Ana, Calif.)+1% penicillin/streptomycin (Invitrogen)+1% Gluta-Max (Invitrogen).

Muscle was triturated through a fire-polished Pasteur pipet until dissociated into myofiber fragments, and medium was transferred to a 14-mL tube. Myofiber fragments were allowed to settle at 37° C. for 10 minutes, after which the supernatant containing interstitial cells was separated from the myofiber fragments and their associated cells. Fragments were washed twice with PBS and then dissociated in PBS+ 0.05% dispase (Invitrogen)+0.0125% collagenase II at 37° C., while shaking, for 30 minutes. The reaction was terminated by addition of FBS (10% of volume), and fibers were triturated three times through a micropipet tip. The preparation was then centrifuged for 1 minute at 500 RPM, and supernatant containing released myofiber-associated cells was separated from settled myofiber debris. Interstitial and myofiber-associated cells were passed through nylon mesh and centrifuged at 1200 RPM. Red blood cells were lysed from interstitial preparations during a 3 minute incubation in 0.15 M ammonium chloride, 0.01M potassium bicarbonate solution on ice.

Antibody staining was performed for 20 minutes on ice in HANKS' Balanced Salt Solution supplemented with 2% FCS and 2 mM EDTA. Prior to FACS analysis, cells were suspended in 1 µg/ml of propidium iodide (PI) to identify and exclude dead ($PI^+$) cells. Populations were sorted using a highly modified Vantage SE (Becton Dickinson Immunocytometry Systems, Mountain View, Calif.), provided by the Stanford University Shared FACS Facility. Flow cytometry data was analyzed using FlowJo (Treestar, San Carlos, Calif.) analysis software.

Cell Culture. 24 hours prior to plating, plates were coated with 0.2% rat-tail collagen and 5 µg/mL natural mouse laminin (Invitrogen). Cells were plated at $1 \times 10^4$ cells/cm 2 in growth medium in either 24-well, 48-well or 96-well tissue culture plates. Growth medium was composed of Ham's F10+20% FBS+5 ng/mL bFGF (Invitrogen)+1% penicillin/streptomycin.24+1% Gluta-Max. bFGF was replaced daily. For co-culture experiments, $1 \times 10^4$ cells of each population were used to initiate cultures. After 5-7 days, cells were passaged by aspiration of medium, washing with PBS, and incubation with PBS for 5 minutes at 37° C. Cells then were replated onto collagen/laminin-coated chamber slides in growth medium for 2 days, and then medium was changed to fusion medium: Opti-MEM (Invitrogen)+1% FBS+1% penicillin/streptomycin+1% Gluta-Max. Cells were kept in fusion medium for 2 days, then medium was aspirated, and cells were fixed with 4% paraformaldehyde for 10 minutes and processed for immunofluorescence.

Muscle Regeneration Assays. Muscle injury was induced by injecting an anesthetized mouse with 25 µl of a 0.3 mg/ml solution of cardiotoxin (from Naja mossambica, Sigma) directly into the TS and/or TA muscles. For harvesting of myofiber-associated and muscle interstitial cells, injured muscle was dissociated (see above) two days following cardiotoxin injection. Myogenic potential was also evaluated in separate experiments in which the TS muscles of $GFP^-$ mice were injured by injection of cardiotoxin, followed 24 hours later by intramuscular delivery of purified GFP+ muscle-resident, BM-resident or splenic populations. $1 \times 10^4$ myofiber-associated cells, $1 \times 10^5$ interstitial cells, $1 \times 10^6$ splenic Mac-1+ and/or $Gr-1^+$ cells, or $1 \times 10^7$ BM cells were injected directly into the site of injury 24 hours after cardiotoxin injection. In these experiments, muscle was harvested 2 weeks after injection and analyzed either by immunostaining of frozen sections or by dissociation, FACS sorting and cell culture.

Parabiosis. Parabiosis surgery was performed exactly as described (Wright et al., supra.), and in accordance with the guidelines established by the Stanford University Administrative Panel for Lab Animal Care for the humane care and use of animals. Parabiotic pairs were housed separately and maintained on standard rodent chow and acidified water ad libitum. The triceps, TA, and/or TS muscles of the outside limbs (those not adjacent to the site of surgical joining) of both partners of the parabiotic pair were injured by injection of cardiotoxin.

Harvesting of tissues for frozen sections. Tissues were dissected and fixed for 2-4 hours in 2% paraformaldehyde at room temperature. Fixed tissues were washed with 1×PBS, cryoprotected by overnight incubation in 30% sucrose, and subsequently quick-frozen in optimum cutting temperature (OCT) compound. OCT-embedded tissues were stored at −80° C. and removed for cryosectioning as needed.

Immunofluorescence analysis. Immunofluorescence analysis was performed on frozen sections of triceps surae muscles. 8 µm frozen sections were cut at −20° C. from OCT-embedded tissues using a 5030 series microtome (Bright Instruments, Huntingdon, England). Sections were air dried overnight at room temperature then stained. Sections were blocked using the M.O.M. blocking kit (Vector Labs, Burlingame, Calif.), the Avidin/Biotin blocking kit (Vector Labs) or 2% normal goat serum, as appropriate. For staining of intracellular antigens, 0.5% Triton X-100 was added to the blocking solution. Sections were stained with primary antibody for 1 hour at room temperature, and with secondary antibody for 30 minutes at room temperature. GFP signal was amplified using anti-GFP Alexa-488 conjugate. Nuclei were labeled with Hoechst 33342 (Molecular Probes). Immunofluorescent labeling was analyzed both by standard fluorescence microscopy, using a Nikon Eclipse E800 microscope, with epifluorescence powered by a super high pressure mercury lamp (Nikon, Tokyo, Japan), and by laser scanning confocal microscopy, using the LSM 510 confocal Laser Scanning microscope (Zeiss, Thornwood, N.Y.) with a Coherent Mira 900 tunable Ti; Sapphire laser for 2 photon excitation, and analyzed with LSM 510 software (Zeiss), provided by the Stanford University Cell Sciences Imaging Facility. For standard epifluorescence, sequential images were acquired using a SPOT RT CCD camera (Diagnostic Instruments, Sterling Heights, Mich.) for Hoechst 33342, Alexa594 and GFP, using UV-2A, HYQ Texas Red, and HYQ FITC (Nikon) filters, respectively, and electronically merged using SPOT RT software (Diagnostic Instruments). For confocal microcopy, images of serial optical sections were recorded every 1.0 µm per vertical step, and analyzed with LSM 510 and Axiovision Viewer software analysis tools (Zeiss). In all cases, appropriate negative and isotype controls demonstrated antigen-specific labeling by each of these antibodies.

RT-PCR analysis. RNA from ~20,000 FACS-sorted cells was extracted with TriZOL (Gibco BRL) according to the manufacturer's instructions. Isolated RNA was resuspended in diethylpyrocarbonate (DEPC)-treated water and incubated with DNaseI (RNase-free, Boehringer) for 20 min. at 37° C. to remove contaminating genomic DNA. Before reverse transcription (RT), DNaseI was inactivated and RNA denatured by incubation at 70° C. for 10 min. After chilling on ice, RNA samples were split equally into two 0.5 mL Eppendorf tubes (3.5 µl per tube), and used for either the RT reaction (+RT), or for a control reaction in which the reverse transcriptase was omitted (−RT). RT master mix per tube contained 4 µl 5×RT buffer, 2 µl 0.1 M dithiothreitol, 1 µl random hexamer (137 pmoles/µl), 8 µl dNTPs (2.5 mM each dNTP), 0.5 µl RNAsin (Promega), and either 1 µl DEPC water (−RT control) or 1 µl Superscript.27 II reverse transcriptase (+RT, Gibco BRL). 16.5 µl of the appropriate (+ or −RT) RT master mix was added to each tube, for a final volume of 20 µl, and RT reactions were performed by incubation at 42° C. Specific cDNA were amplified from the RT reactions by hot-start PCR using 3.3 µl per tube of the RT reaction as template and a total volume of 50 µl per reaction. PCR master mix per tube contained 5 µl 10× PCR buffer, 5 µl 25 mM MgCl2, 4 µl dNTPs (2.5 mM each), 1.5 µl each primer (from a 16.7 µM stock), 0.25 µl Taq polymerase, 29.5 µl water, and 3.3 µl template (RT reaction). PCR parameters were optimized for each primer set and PCR amplification was performed for 40 cycles of 95° C., 30 sec.→Ta, 30 sec.→72° C., 30 sec., where Ta is the optimal annealing temperature for the primer set, listed below.

| Target | Forward primer | Reverse primer | Annealing temp. | Product size (bp) |
|---|---|---|---|---|
| Myf5 | GGAGATCCTCAGGAATGCCATCCGC | TGCTGTTCTTTCGGGACCAGACAGG | 66 | 178 |
| MyoD | GCTCTGATGGCATGATGGATTACAGCG | ATGCTGGACAGGCAGTCGAGGC | 68 | 145 |
| desmin | ACATGGCTATCAGGACAACATTGCG | TGCTGTGTAGCCTCGCTGACA | 62 | 315 |
| vimentin | GATTTCTCTCTGCCTCTGCCAAC | GTGATGCTGAGAAGTCTCAT | 62 | 157 |
| Pax-7 | GAAAGCCAAACACAGCATCGA | ACCCTGATGCATGGTTGATGG | 65 | 466 |
| β-actin | TGGGCCGCTCTAGGCACC | CTCTTTGATGTCACGCACG | 65-70 | 540 |

Example 2

Further Characterization of Myogenic Colony Forming Cells

Myofiber associated cells were obtained by dissociation into single myofibers as described in Example 1. The cells were stained with antibodies specific for markers of interest, and tested for their ability to form myogenic colonies. The myogenic CFC were found to positively express: CD34, CXCR4, c-met (HGF-receptor), and beta1-integrin. The myogenic CFC were negative for expression of: CD45, Sca-1, Mac-1, B220, CD3, Gr-1, Thy-1, c-Kit, CD13, CD44, CD71, CD105, Flk-1, Flk-2, alpha1-integrin, and alpha6-integrin.

It was found that approximately 10% of CD45$^-$Sca-1$^-$CD34$^+$ cells were myogenic CFC. In the CD45$^-$Sca-1$^-$Mac-1$^-$CD34$^+$ cell population, 18.4% give myogenic CFC. In the CD45$^-$-Sca-1$^-$CXCR4$^+$ population, approximately 24% of the cells gave rise to myogenic colonies.

Cells that were sorted for the phenotype of myofiber associated, CD45$^-$Sca-1$^-$Mac-1$^-$ CXCR4$^+$Beta1-integrin$^+$ formed round myogenic colonies in 54/109 wells (49.5%+/−5.5%). No other phenotypes were seen among these clone sorted cells. A similar cell population that was negative for expression of CXCR4 (CD45$^-$Sca-1$^-$Mac-1$^-$CXCR4$^-$Beta1-integrin$^+$) formed no colonies out of 525 wells. Populations of myofiber associated CD45$^+$Sca-1$^+$Mac-1$^+$ cells also failed to form myogenic colonies, out of 850 wells no colonies were observed.

What is claimed is:

1. A method of enrichment for a composition comprising a population of human or mouse myogenic progenitor cells, wherein at least 80% of the cells in said population are myofiber associated, CD45−, Sca-1−, Mac-1−, CXCR4+, and β1-integrin+; the method comprising:
dissociating human or mouse muscle tissue to provide a population of myofiber associated cells;
combining reagents that specifically recognize Mac-1, CXCR4, β-1integrin, and CD45 respectively, with said population of myofiber associated cells;
selecting for those cells that are CD45−, Sca-1−, Mac-1−, CXCR4+, and β1-integrin +; wherein said selected population of cells are capable of forming myogenic colonies.

2. The method according to claim 1, wherein said cells are human cells.

3. A composition obtained by the method of claim 1.

4. The composition of myogenic progenitor cells according to claim 3, wherein said cells are endogenous muscle cells.

5. The composition of myogenic progenitor cells according to claim 3, wherein said cells are human cells.

6. A method for regenerating skeletal muscle in a mouse, the method comprising:
introducing into said mouse the composition of claim 3, thereby skeletal muscle is regenerated in said mouse.

* * * * *

SEQUENCE LISTING

<160> NUMBER OF SEQ ID NOS: 12

<210> SEQ ID NO 1
<211> LENGTH: 25
<212> TYPE: DNA
<213> ORGANISM: mouse

<400> SEQUENCE: 1
ggagatcctc aggaatgcca tccgc         25

<210> SEQ ID NO 2
<211> LENGTH: 25
<212> TYPE: DNA
<213> ORGANISM: mouse

<400> SEQUENCE: 2
tgctgttctt cgggaccag acagg         25

<210> SEQ ID NO 3
<211> LENGTH: 27
<212> TYPE: DNA
<213> ORGANISM: mouse

<400> SEQUENCE: 3
gctctgatgg catgatggat tacagcg         27

<210> SEQ ID NO 4
<211> LENGTH: 22
<212> TYPE: DNA

<213> ORGANISM: mouse

<400> SEQUENCE: 4
atgctggaca ggcagtcgag gc                                    22

<210> SEQ ID NO 5
<211> LENGTH: 25
<212> TYPE: DNA
<213> ORGANISM: mouse

<400> SEQUENCE: 5
acatggctat caggacaaca ttgcg                                 25

<210> SEQ ID NO 6
<211> LENGTH: 21
<212> TYPE: DNA
<213> ORGANISM: mouse

<400> SEQUENCE: 6
tgctgtgtag cctcgctgac a                                     21

<210> SEQ ID NO 7
<211> LENGTH: 23
<212> TYPE: DNA
<213> ORGANISM: mouse

<400> SEQUENCE: 7
gatttctctc tgcctctgcc aac                                   23

<210> SEQ ID NO 8
<211> LENGTH: 20
<212> TYPE: DNA
<213> ORGANISM: mouse

<400> SEQUENCE: 8
gtgatgctga gaagtctcat                                       20

<210> SEQ ID NO 9
<211> LENGTH: 21
<212> TYPE: DNA
<213> ORGANISM: mouse

<400> SEQUENCE: 9
gaaagccaaa cacagcatcg a                                     21

<210> SEQ ID NO 10
<211> LENGTH: 21
<212> TYPE: DNA
<213> ORGANISM: mouse

<400> SEQUENCE: 10
accctgatgc atggttgatg g                                     21

<210> SEQ ID NO 11
<211> LENGTH: 18
<212> TYPE: DNA
<213> ORGANISM: mouse

<400> SEQUENCE: 11
tgggccgctc taggcacc                                         18

<210> SEQ ID NO 12
<211> LENGTH: 19

```
-continued

<212> TYPE: DNA
<213> ORGANISM: mouse

<400> SEQUENCE: 12
ctctttgatg tcacgcacg                                                    19
```